United States Patent
Hully et al.

(10) Patent No.: US 8,758,996 B2
(45) Date of Patent: Jun. 24, 2014

(54) OPTIMIZED PROBES AND PRIMERS AND METHODS OF USING SAME FOR THE BINDING, DETECTION, DIFFERENTIATION, ISOLATION AND SEQUENCING OF INFLUENZA A; INFLUENZA B; NOVEL INFLUENZA A/H1N1; AND A NOVEL INFLUENZA A/H1N1 RNA SEQUENCE MUTATION ASSOCIATED WITH OSELTAMIVIR RESISTANCE

(75) Inventors: James R. Hully, Mundelein, IL (US); David L. Dolinger, Medway, MA (US); Alice A. Jacobs, Cambridge, MA (US); Damien Slater, Roslindale, MA (US); Heather L. B. Kiefer, Westford, MA (US); Chesley Leslin, Boston, MA (US); Juan Manuel Anzola, Waltham, MA (US)

(73) Assignee: Intelligent Medical Devices, Inc., Cambridge, MA (US)

( * ) Notice: Subject to any disclaimer, the term of this patent is extended or adjusted under 35 U.S.C. 154(b) by 0 days.

(21) Appl. No.: 12/887,193

(22) Filed: Sep. 21, 2010

(65) Prior Publication Data

US 2011/0250583 A1 Oct. 13, 2011

Related U.S. Application Data

(60) Provisional application No. 61/244,435, filed on Sep. 21, 2009, provisional application No. 61/251,616, filed on Oct. 14, 2009.

(51) Int. Cl.
*C12Q 1/68* (2006.01)

(52) U.S. Cl.
USPC .......................................................... 435/6.1

(58) Field of Classification Search
None
See application file for complete search history.

(56) References Cited

U.S. PATENT DOCUMENTS

| 2007/0259337 | A1 * | 11/2007 | Hully et al. ................. 435/5 |
| 2008/0293040 | A1 | 11/2008 | Kawaoka et al. |
| 2009/0048439 | A1 | 2/2009 | Weisburg et al. |

FOREIGN PATENT DOCUMENTS

| WO | WO 2004028471 A2 * | 4/2004 |
| WO | WO 2004045365 A2 * | 6/2004 |
| WO | WO 2004057021 A2 * | 7/2004 |
| WO | WO 2005/005658 | 1/2005 |

OTHER PUBLICATIONS

GenBank record AF255370.1, GI: 13274619, Influenza A virus membrane matrix protein M1 and membrane ion channel M2 (M) gene, complete cds, Mar. 12, 2001. Accessed from http://www.ncbi.nlm.nih.gov/nuccore/13274619?sat=34&satkey=194403 on Sep. 6, 2012. Two pages.*
van Elden et al., 2001, Journal of Clinical Microbiology, vol. 39, pp. 196-200.*
International Preliminary Report on Patentability for PCT/US2010/049694 DTD Mar. 27, 2012.
PCT International Search Report—(PCT/US10/49694) Date of Mailing Mar. 25, 2011.
Panning et al., "Detection of influenza A (H1N1)v virus by real-time RT-PCR", Euro Surveill. 2009, vol. 14, pp. 1-6.

* cited by examiner

*Primary Examiner* — Anne Gussow
*Assistant Examiner* — Mindy G Brown
(74) *Attorney, Agent, or Firm* — Foley & Lardner LLP; Michael Morency

(57) ABSTRACT

Described herein are primers and probes useful for the binding, detecting, differentiating, isolating, and sequencing of influenza A, influenza B, 2009 influenza A/H1N1, and a 2009 influenza A/H1N1 RNA sequence mutation associated with oseltamivir resistance.

12 Claims, No Drawings

SEQUENCE LISTING

```
<160> NUMBER OF SEQ ID NOS: 369

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gctctcatgg aatggctaaa gac                                            23

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
```

```
tcaccgtgcc cagtgagcga g                                              21
```

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3

```
gcattttgga caaagcgtct acg                                            23
```

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4

```
tggatacaag tccttatcaa ctctg                                          25
```

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5

```
tcgaagagtg agttgaggat ccg                                            23
```

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

```
tgctcttgac caaattggga t                                              21
```

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

```
gttgctaaac ttgttgctac tga                                            23
```

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8

```
ttgaggatcc gatggccatc tt                                             22
```

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gctgctcgaa ttggcttt                                                    18

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tggtgataat cggtgctctt g                                                21

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gctaaacttg ttgctactga tga                                              23

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tcggtgctct tgaccaaatt                                                  20

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tacaagtcct tatcaactct gcat                                             24

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cttgttgcta aacttgttgc                                                  20

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
tcggatcctc aactcactct tcg                                             23

<210> SEQ ID NO 16
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tcagctgctc gaattg                                                     16

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
tcggatcctc aattcactct tcg                                             23

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tttcagctgc tcgaattg                                                   18

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
catcggatcc tcaattcact cttcg                                           25

<210> SEQ ID NO 20
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
aatgaaggac attcaaagcc aattcgagca gctga                                35

```
<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cttgaccaaa ttgggataag actcc                                              25

<210> SEQ ID NO 22
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
caaagccaat tcgagcagct gaaactgcg                                          29

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gtgataatcg gtgctcttga ccaaa                                              25

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
aacatgacca caacacaaat tgagg                                              25

<210> SEQ ID NO 25
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 25
tcctgcttca aagtttatag tggcattggt tgctc                                   35

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gtaatcaagg gctctttgcc atgaa                                              25

<210> SEQ ID NO 27
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tcacaacaca aattgaggtg ggt                                          23

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ttggccaggg tagtcaaggg                                              20

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ctgtttaggc ggttttgacc ag                                           22

<210> SEQ ID NO 30
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gctagttaaa aaggaaatt catacc                                        26

<210> SEQ ID NO 31
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 31
cagcaaatcc tacattaatg ataaagggaa agaag                             35

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tggtcagcac tagtagatgg a                                            21

<210> SEQ ID NO 33
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tggagcaaaa agcttctaca aaaa                                              24

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
catatgcatc tgcattctga taga                                              24

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tttgttggtc agcactagta gat                                               23

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gatagtcccc aagacaagtt catgg                                             25

<210> SEQ ID NO 37
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 37
cattaatgta ggatttgctg agctttggg                                         29

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gatggtgaat gccccatagc ac                                                22

<210> SEQ ID NO 39
<211> LENGTH: 24
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 39
caagttcatg gcccaatcat gact                                          24

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 40
acaaaggtgt aacggcagca tgtcc                                         25

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
cactagaaga tggatggtga atgcc                                         25

<210> SEQ ID NO 42
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
aaagggaaag aagttctcgt gctat                                         25

<210> SEQ ID NO 43
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 43
actagtagat ggatggtgaa tgcccc                                        26

<210> SEQ ID NO 44
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gctatttccg gcttgaactt ctt                                           23

<210> SEQ ID NO 45
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 45
tcatatccaa agctcagcaa atcct                                          25

<210> SEQ ID NO 46
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 46
gcattctgat agagactttg ttggtcagc                                      29

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gctgtatctt gatgtcccca caaaa                                          25

<210> SEQ ID NO 48
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gtcgaaatga atgcccctaa ttatc                                          25

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 49
agccatgcca gttatccctg c                                              21

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
cgtggattgt ctccgaaa                                                  18

<210> SEQ ID NO 51
<211> LENGTH: 25
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 51
gtcgaaatga atgcccctaa ttacc                                           25

<210> SEQ ID NO 52
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
cgaaatgaat gcccctaatt atcac                                           25

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
tgtgcatgtg taaatggttc                                                 20

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 54
agcattcctc atagtgat                                                   18

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gaatcaggat aacaggagca t                                               21

<210> SEQ ID NO 56
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 56 aatgcccta attatac                                                     17

<210> SEQ ID NO 57
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 57
cttcagaata gaaaagggaa agatagtc                                           28

<210> SEQ ID NO 58
<211> LENGTH: 38
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 58
ttggcgtttc atagtaataa ttaggggatt aacgccaa                                 38

<210> SEQ ID NO 59
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ttcgagccat gccagtt                                                       17

<210> SEQ ID NO 60
<211> LENGTH: 38
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 60
aaccgcaacc ctaattatca ctatgaggaa ttgcggtt                                 38

<210> SEQ ID NO 61
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
tcatacaaga tcttcagaat agaaaagg                                           28

<210> SEQ ID NO 62
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
atttcactag aatcaggata acaggag                                            27

<210> SEQ ID NO 63
<211> LENGTH: 38
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 63
aaccgcaacc ctaattatta ctatgaggaa ttgcggtt                              38

<210> SEQ ID NO 64
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 64
attcctcata gtaataatta gggg                                             24

<210> SEQ ID NO 65
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 65
attcctcata gtgataatta gggg                                             24

<210> SEQ ID NO 66
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 66
attcctcata gtgataatta gg                                               22

<210> SEQ ID NO 67
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 67
attcctcata gtaataatta ggg                                              23

<210> SEQ ID NO 68
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
caatgcaacg ttctccaac                                                   19

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      probe -continued

```
<400> SEQUENCE: 69
tgcaggatgc agcgccttac                                              20

<210> SEQ ID NO 70
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
taacggttgc ttgttcagc                                               19

<210> SEQ ID NO 71
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
aatcttcgta aaacgttcgt gtc                                          23

<210> SEQ ID NO 72
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 72
cacttttacc gtggtgtcga tgtcaaac                                     28

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
cgaagagatt gtcaacaggt                                              20

<210> SEQ ID NO 74
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
gtccgagacc aatgtgc                                                 17

<210> SEQ ID NO 75
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 75
``` ccgttccct a caacgagcct aaattcata                                    29

<210> SEQ ID NO 76
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
caggcagccc gatctatt                                                 18

<210> SEQ ID NO 77
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
tatgccccaa actagcagaa taca                                          24

<210> SEQ ID NO 78
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
tatgccccaa actagcagaa taca                                          24

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
gtatctgacc aacaccacca t                                             21

<210> SEQ ID NO 80
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
gctgtgtgaa ccaacaataa tagaa                                         25

<210> SEQ ID NO 81
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81

```
acagagatag tgtatctgac caac                                          24
```

<210> SEQ ID NO 82
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82

```
tgctgtgtga accaacaata ataga                                         25
```

<210> SEQ ID NO 83
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83

```
acagagatag tgtatctgac caac                                          24
```

<210> SEQ ID NO 84
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84

```
acagagatag tgtatctgac caac                                          24
```

<210> SEQ ID NO 85
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85

```
tgctgtgtga accaacaata atag                                          24
```

<210> SEQ ID NO 86
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86

```
tgaccaacac caccat                                                   16
```

<210> SEQ ID NO 87
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87

```
acagagatag tgtatctgac caac                                          24
```

<210> SEQ ID NO 88
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
ggcaaaagct gcatcaat                                                  18

<210> SEQ ID NO 89
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
tggtcaaagc cgcaatgt                                                  18

<210> SEQ ID NO 90
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
tggtcaaagc cgcaatg                                                   17

<210> SEQ ID NO 91
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
gctgtgtgaa ccaacaataa taga                                           24

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
gtatctgacc aacaccacca t                                              21

<210> SEQ ID NO 93
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
gctgtgtgaa ccaacaataa taga                                           24

<210> SEQ ID NO 94
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 94
gtatctgacc aacaccacca t        21

<210> SEQ ID NO 95
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 95
gctgtgtgaa ccaacaataa tagaa        25

<210> SEQ ID NO 96
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 96
tgctgtgtga accaacaata ataga        25

<210> SEQ ID NO 97
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 97
gtatctgacc aacaccacca t        21

<210> SEQ ID NO 98
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 98
tgctgtgtga accaacaata ataga        25

<210> SEQ ID NO 99
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 99
tgctgtgtga accaacaata atag        24

```
<210> SEQ ID NO 100
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
ggtgctttta tgtggagttg ataag                                            25

<210> SEQ ID NO 101
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 101
ccaccagcgg aaagcc                                                      16

<210> SEQ ID NO 102
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 102
ccaccagcgg aaagcc                                                      16

<210> SEQ ID NO 103
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 103
ccaccagcgg aaagcc                                                      16

<210> SEQ ID NO 104
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 104
ccaccagcgg aaagcc                                                      16

<210> SEQ ID NO 105
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 105
ccaccagcgg aaagcc                                                      16

<210> SEQ ID NO 106
```

```
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 106
ccaccagcgg aaagcc                                                       16

<210> SEQ ID NO 107
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 107
ccaccagcgg aaagcc                                                       16

<210> SEQ ID NO 108
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 108
ccaccagcgg aaagcc                                                       16

<210> SEQ ID NO 109
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 109
ccaccagcgg aaagcc                                                       16

<210> SEQ ID NO 110
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 110
ccaccagcgg aaagcc                                                       16

<210> SEQ ID NO 111
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 111
ccaccagcgg aaagcc                                                       16

<210> SEQ ID NO 112
<211> LENGTH: 34
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 112
tatgtacctg aggtgccaca aaacacaaca atac                              34

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 113
cttgtcaccc agatgtcccc                                              20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 114
cttgtcaccc agatgtcccc                                              20

<210> SEQ ID NO 115
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 115
agagaaggaa atatgcccca aact                                         24

<210> SEQ ID NO 116
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 116
agagaaggaa atatgcccca aact                                         24

<210> SEQ ID NO 117
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 117
ccaccataga gaaggaaata tgccccaaac t                                 31

<210> SEQ ID NO 118
<211> LENGTH: 24
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 118
agagaaggaa atatgcccca aact                                          24

<210> SEQ ID NO 119
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 119
ccaccataga gaaggaaata tgccccaaac t                                  31

<210> SEQ ID NO 120
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 120
ccaccataga gaaggaaata tgccccaaac t                                  31

<210> SEQ ID NO 121
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 121
agagaaggaa atatgcccca aact                                          24

<210> SEQ ID NO 122
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 122
agagaaggaa atatgcccca aact                                          24

<210> SEQ ID NO 123
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 123
ccaccataga gaaggaaata tgccccaaac t                                  31

<210> SEQ ID NO 124
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 124
tcgcatgaca cataaggttc t                                              21

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
tcgcatgaca cataaggttc t                                              21

<210> SEQ ID NO 126
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
tgtcacccag atgtcc                                                    16

<210> SEQ ID NO 127
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
tgtcacccag atgtcc                                                    16

<210> SEQ ID NO 128
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
tgtcacccag atgtcc                                                    16

<210> SEQ ID NO 129
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
tgtcacccag atgtcc                                                    16

<210> SEQ ID NO 130
<211> LENGTH: 16
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 130
tgtcacccag atgtcc                                                        16

<210> SEQ ID NO 131
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
tgtcacccag atgtcc                                                        16

<210> SEQ ID NO 132
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
tgtcacccag atgtcc                                                        16

<210> SEQ ID NO 133
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
tgtcacccag atgtcc                                                        16

<210> SEQ ID NO 134
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
tgtcacccag atgtcc                                                        16

<210> SEQ ID NO 135
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
tcgatgtccg ccccat                                                        16

<210> SEQ ID NO 136
<211> LENGTH: 22
<212> TYPE: DNA
<213> ORGANISM: Artificial Sequence
<220> FEATURE:
<223> OTHER INFORMATION: Description of Artificial Sequence: Synthetic -continued primer

<400> SEQUENCE: 136
ttgtttagtg ttgttccctg tc                                              22

<210> SEQ ID NO 137
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
ttgtttagtg ttgttccctg tc                                              22

<210> SEQ ID NO 138
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
tcgcatgaca cataaggttc tc                                              22

<210> SEQ ID NO 139
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
tcgcatgaca cataaggttc tc                                              22

<210> SEQ ID NO 140
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
tcgcatgaca cataaggttc tc                                              22

<210> SEQ ID NO 141
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
tcgcatgaca cataaggttc tc                                              22

<210> SEQ ID NO 142
<211> LENGTH: 22
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 142
tcgcatgaca cataaggttc tc                                          22

<210> SEQ ID NO 143
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
tcgcatgaca cataaggttc tc                                          22

<210> SEQ ID NO 144
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
tcgcatgaca cataaggttc tc                                          22

<210> SEQ ID NO 145
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
tcgcatgaca cataaggttc tc                                          22

<210> SEQ ID NO 146
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
tcgcatgaca cataaggttc tc                                          22

<210> SEQ ID NO 147
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
gccatgagcc tgttcca                                                17

<210> SEQ ID NO 148
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 148
gactgctagc ttcatttaca atgg                                            24

<210> SEQ ID NO 149
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
aactgctagc ttcatttaca atgg                                            24

<210> SEQ ID NO 150
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
ctactgctag cttcatttac aatgg                                           25

<210> SEQ ID NO 151
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
gactgctagc ttcatttaca atgg                                            24

<210> SEQ ID NO 152
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
aactgctagc ttcatttaca atgg                                            24

<210> SEQ ID NO 153
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
ctactgctag cttcatttac aatgg                                           25

<210> SEQ ID NO 154
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
```
gactgctagc ttcatttaca atgg                                              24

<210> SEQ ID NO 155
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
aactgctagc ttcatttaca atgg                                              24

<210> SEQ ID NO 156
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
ctactgctag cttcatttac aatgg                                             25

<210> SEQ ID NO 157
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
gactgctagc ttcatttaca atgg                                              24

<210> SEQ ID NO 158
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
aactgctagc ttcatttaca atgg                                              24

<210> SEQ ID NO 159
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
ctactgctag cttcatttac aatgg                                             25

<210> SEQ ID NO 160
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
gactgctagc ttcatttaca atgg                                              24

<210> SEQ ID NO 161
<211> LENGTH: 24
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 161
aactgctagc ttcatttaca atgg                                              24

<210> SEQ ID NO 162
<211> LENGTH: 25
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 162
ctactgctag cttcatttac aatgg                                             25

<210> SEQ ID NO 163
<211> LENGTH: 24
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 163
gactgctagc ttcatttaca atgg                                              24

<210> SEQ ID NO 164
<211> LENGTH: 24
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 164
aactgctagc ttcatttaca atgg                                              24

<210> SEQ ID NO 165
<211> LENGTH: 25
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 165
ctactgctag cttcatttac aatgg                                             25

<210> SEQ ID NO 166
<211> LENGTH: 24
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 166
gactgctagc ttcatttaca atgg                                              24

<210> SEQ ID NO 167
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
aactgctagc ttcatttaca atgg                                            24

<210> SEQ ID NO 168
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
ctactgctag cttcatttac aatgg                                           25

<210> SEQ ID NO 169
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
aactgctagc ttcatttaca atgg                                            24

<210> SEQ ID NO 170
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
gactgctagc ttcatttaca atgg                                            24

<210> SEQ ID NO 171
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
ctactgctag cttcatttac aatgg                                           25

<210> SEQ ID NO 172
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
gactgctagc ttcatttaca atgg                                            24

<210> SEQ ID NO 173
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
aactgctagc ttcatttaca atgg                                          24

<210> SEQ ID NO 174
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
ctactgctag cttcatttac aatgg                                         25

<210> SEQ ID NO 175
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
aactgctagc ttcatttaca atgg                                          24

<210> SEQ ID NO 176
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
gactgctagc ttcatttaca atgg                                          24

<210> SEQ ID NO 177
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
ctactgctag cttcatttac aatgg                                         25

<210> SEQ ID NO 178
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
aactgctagc ttcatttaca atgg                                          24

```
<210> SEQ ID NO 179
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
gactgctagc ttcatttaca atgg                                          24

<210> SEQ ID NO 180
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
ctactgctag cttcatttac aatgg                                         25

<210> SEQ ID NO 181
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
gactgctagc ttcatttaca atgg                                          24

<210> SEQ ID NO 182
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
aactgctagc ttcatttaca atgg                                          24

<210> SEQ ID NO 183
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
ctactgctag cttcatttac aatgg                                         25

<210> SEQ ID NO 184
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
aactgctagc ttcatttaca atgg                                          24

<210> SEQ ID NO 185
```

-continued

```
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
gactgctagc ttcatttaca atgg                                          24

<210> SEQ ID NO 186
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
ctactgctag cttcatttac aatgg                                         25

<210> SEQ ID NO 187
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
aactgctagc ttcatttaca atgg                                          24

<210> SEQ ID NO 188
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
gactgctagc ttcatttaca atgg                                          24

<210> SEQ ID NO 189
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
ctactgctag cttcatttac aatgg                                         25

<210> SEQ ID NO 190
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
aactgctagc ttcatttaca atgg                                          24

<210> SEQ ID NO 191
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
gactgctagc ttcatttaca atgg                                          24

<210> SEQ ID NO 192
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 192
ctactgctag cttcatttac aatgg                                         25

<210> SEQ ID NO 193
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
gactgctagc ttcatttaca atgg                                          24

<210> SEQ ID NO 194
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
aactgctagc ttcatttaca atgg                                          24

<210> SEQ ID NO 195
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
ctactgctag cttcatttac aatgg                                         25

<210> SEQ ID NO 196
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
gactgctagc ttcatttaca atgg                                          24

<210> SEQ ID NO 197
<211> LENGTH: 24
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 197
aactgctagc ttcatttaca atgg                                           24

<210> SEQ ID NO 198
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
ctactgctag cttcatttac aatgg                                          25

<210> SEQ ID NO 199
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
ctactgctag cttcatttac aatgg                                          25

<210> SEQ ID NO 200
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
ctactgctag cttcatttac aatgg                                          25

<210> SEQ ID NO 201
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
ctactgctag cttcatttac aatgg                                          25

<210> SEQ ID NO 202
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
ctactgctag cttcatttac aatgg                                          25

<210> SEQ ID NO 203
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 203
ctactgctag cttcatttac aatgg                                          25

<210> SEQ ID NO 204
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 204
gactgctagc ttcatttaca atgg                                           24

<210> SEQ ID NO 205
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
aactgctagc ttcatttaca atgg                                           24

<210> SEQ ID NO 206
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
aactgctagc ttcatttaca atgg                                           24

<210> SEQ ID NO 207
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
gactgctagc ttcatttaca atgg                                           24

<210> SEQ ID NO 208
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
ctactgctag cttcatttac aatgg                                          25

<210> SEQ ID NO 209
<211> LENGTH: 25
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 209
ctactgctag cttcatttac aatgg            25

<210> SEQ ID NO 210
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210
gactgctagc ttcatttaca atgg             24

<210> SEQ ID NO 211
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
aactgctagc ttcatttaca atgg             24

<210> SEQ ID NO 212
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
ctactgctag cttcatttac aatgg            25

<210> SEQ ID NO 213
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
aactgctagc ttcatttaca atgg             24

<210> SEQ ID NO 214
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
gactgctagc ttcatttaca atgg             24

<210> SEQ ID NO 215
<211> LENGTH: 25
<212> TYPE: DNA
<213> ORGANISM: Artificial Sequence
<220> FEATURE:
<223> OTHER INFORMATION: Description of Artificial Sequence: Synthetic -continued

```
      primer

<400> SEQUENCE: 215
ctactgctag cttcatttac aatgg                                               25

<210> SEQ ID NO 216
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
gactgctagc ttcatttaca atgg                                                24

<210> SEQ ID NO 217
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
aactgctagc ttcatttaca atgg                                                24

<210> SEQ ID NO 218
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
ctactgctag cttcatttac aatgg                                               25

<210> SEQ ID NO 219
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 219
ttttggacca tgaaacaata ctatctacaa gcctc                                    35

<210> SEQ ID NO 220
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 220
ttttggacca tgaaacaata ctatctacaa gcctc                                    35

<210> SEQ ID NO 221
<211> LENGTH: 35
<212> TYPE: DNA
<213> ORGANISM: Artificial Sequence
<220> FEATURE:
<223> OTHER INFORMATION: Description of Artificial Sequence: Synthetic
      probe
```

<400> SEQUENCE: 221
ttttggacca tgaaacaata ctatctacaa gcctc          35

<210> SEQ ID NO 222
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 222
ttttggacca tgaaacaata ctatctacaa gcctc          35

<210> SEQ ID NO 223
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 223
ttttggacca tgaaacaata ctatctacaa gcctc          35

<210> SEQ ID NO 224
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 224
ttttggacca tgaaacaata ctatctacaa gcctc          35

<210> SEQ ID NO 225
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 225
ttttggacca tgaaacaata ctatctacaa gcct          34

<210> SEQ ID NO 226
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 226
ttttggacca tgaaacaata ctatctacaa gcct          34

<210> SEQ ID NO 227
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 227
ttttggacca tgaaacaata ctatctacaa gcct                                   34

<210> SEQ ID NO 228
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 228
ttttggacca tgaaacaata ctatctacaa gcct                                   34

<210> SEQ ID NO 229
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 229
ttttggacca tgaaacaata ctatctacaa gcct                                   34

<210> SEQ ID NO 230
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 230
ttttggacca tgaaacaata ctatctacaa gcct                                   34

<210> SEQ ID NO 231
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 231
ttctttggac catgaaacaa tactatctac aagcc                                  35

<210> SEQ ID NO 232
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 232
ttctttggac catgaaacaa tactatctac aagcc                                  35

<210> SEQ ID NO 233
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 233
```
ttctttggac catgaaacaa tactatctac aagcc                              35

<210> SEQ ID NO 234
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 234
ttctttggac catgaaacaa tactatctac aagcc                              35

<210> SEQ ID NO 235
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 235
ttctttggac catgaaacaa tactatctac aagcc                              35

<210> SEQ ID NO 236
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 236
ttctttggac catgaaacaa tactatctac aagcc                              35

<210> SEQ ID NO 237
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 237
ttctttggac catgaaacaa tactatctac aagcc                              35

<210> SEQ ID NO 238
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 238
ttctttggac catgaaacaa tactatctac aagcc                              35

<210> SEQ ID NO 239
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 239
ttctttggac catgaaacaa tactatctac aagcc                                35

<210> SEQ ID NO 240
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 240
ttctttggac catgaaacaa tactatctac aagca                                35

<210> SEQ ID NO 241
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 241
ttctttggac catgaaacaa tactatctac aagca                                35

<210> SEQ ID NO 242
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 242
ttctttggac catgaaacaa tactatctac aagca                                35

<210> SEQ ID NO 243
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 243
tctttggacc atgaaacaat actatctaca agcct                                35

<210> SEQ ID NO 244
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 244
tctttggacc atgaaacaat actatctaca agcct                                35

<210> SEQ ID NO 245
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 245
tctttggacc atgaaacaat actatctaca agcct                                35

<210> SEQ ID NO 246
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 246
tctttggacc atgaaacaat actatctaca agcct                                35

<210> SEQ ID NO 247
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 247
tctttggacc atgaaacaat actatctaca agcct                                35

<210> SEQ ID NO 248
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 248
tctttggacc atgaaacaat actatctaca agcct                                35

<210> SEQ ID NO 249
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 249
tacaaatgca ttctgactcc tgggtcctga                                      30

<210> SEQ ID NO 250
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 250
tacaaatgca ttctgactcc tgggtcctga                                      30

<210> SEQ ID NO 251
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 251
tacaaatgca ttctgactcc tgggtcctga                                      30

<210> SEQ ID NO 252
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 252
tacaaatgca ttctgactcc tgggtcctg                                    29

<210> SEQ ID NO 253
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 253
tacaaatgca ttctgactcc tgggtcctg                                    29

<210> SEQ ID NO 254
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 254
tacaaatgca ttctgactcc tgggtcctg                                    29

<210> SEQ ID NO 255
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 255
ctttggacca tgaaacaata ctatctacaa gcatc                             35

<210> SEQ ID NO 256
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 256
ctttggacca tgaaacaata ctatctacaa gcatc                             35

<210> SEQ ID NO 257
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 257
ctttggacca tgaaacaata ctatctacaa gcatc                             35

```
<210> SEQ ID NO 258
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 258
cgcattctga ctcctgggtc ctga                                              24

<210> SEQ ID NO 259
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 259
cgcattctga ctcctgggtc ctga                                              24

<210> SEQ ID NO 260
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 260
cgcattctga ctcctgggtc ctga                                              24

<210> SEQ ID NO 261
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 261
cgcattctga ctcctgggtc ctg                                               23

<210> SEQ ID NO 262
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 262
cgcattctga ctcctgggtc ctg                                               23

<210> SEQ ID NO 263
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 263
cgcattctga ctcctgggtc ctg                                               23

<210> SEQ ID NO 264
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 264
cgcattctga ctcctgggtc ct                                              22

<210> SEQ ID NO 265
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 265
cgcattctga ctcctgggtc ct                                              22

<210> SEQ ID NO 266
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 266
cgcattctga ctcctgggtc ct                                              22

<210> SEQ ID NO 267
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 267
cattctgact cctgggtcct gaggata                                         27

<210> SEQ ID NO 268
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 268
cattctgact cctgggtcct gaggata                                         27

<210> SEQ ID NO 269
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 269
cattctgact cctgggtcct gaggata                                         27

<210> SEQ ID NO 270
<211> LENGTH: 35
```

<212> TYPE: DNA
<213> ORGANISM: Artificial Sequence
<220> FEATURE:
<223> OTHER INFORMATION: Description of Artificial Sequence: Synthetic
      probe

<400> SEQUENCE: 270
agcttgtaga tagtattgtt tcatggtcca aagaa                              35

<210> SEQ ID NO 271
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 271
agcttgtaga tagtattgtt tcatggtcca aagaa                              35

<210> SEQ ID NO 272
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 272
agcttgtaga tagtattgtt tcatggtcca aagaa                              35

<210> SEQ ID NO 273
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 273
agcttgtaga tagtattgtt tcatggtcca aagaa                              35

<210> SEQ ID NO 274
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 274
agcttgtaga tagtattgtt tcatggtcca aagaa                              35

<210> SEQ ID NO 275
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 275
aaggcttgta gatagtattg tttcatggtc caaag                              35

<210> SEQ ID NO 276
<211> LENGTH: 35
<212> TYPE: DNA

<213> ORGANISM: Artificial Sequence
<220> FEATURE:
<223> OTHER INFORMATION: Description of Artificial Sequence: Synthetic
      probe

<400> SEQUENCE: 276
aaggcttgta gatagtattg tttcatggtc caaag                              35

<210> SEQ ID NO 277
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 277
aaggcttgta gatagtattg tttcatggtc caaag                              35

<210> SEQ ID NO 278
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 278
aaggcttgta gatagtattg tttcatggtc caaag                              35

<210> SEQ ID NO 279
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 279
aaggcttgta gatagtattg tttcatggtc caaag                              35

<210> SEQ ID NO 280
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 280
aaggcttgta gatagtattg tttcatggtc caaag                              35

<210> SEQ ID NO 281
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 281
aaggcttgta gatagtattg tttcatggtc caaag                              35

<210> SEQ ID NO 282
<211> LENGTH: 35
<212> TYPE: DNA
<213> ORGANISM: Artificial Sequence

```
<220> FEATURE:
<223> OTHER INFORMATION: Description of Artificial Sequence: Synthetic
      probe

<400> SEQUENCE: 282
aaggcttgta gatagtattg tttcatggtc caaag                              35

<210> SEQ ID NO 283
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 283
aaggcttgta gatagtattg tttcatggtc caaag                              35

<210> SEQ ID NO 284
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 284
aaggcttgta gatagtattg tttcatggtc caaag                              35

<210> SEQ ID NO 285
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 285
aaggcttgta gatagtattg tttcatggtc caaag                              35

<210> SEQ ID NO 286
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 286
aaggcttgta gatagtattg tttcatggtc caaag                              35

<210> SEQ ID NO 287
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 287
aaggcttgta gatagtattg tttcatggtc caaag                              35

<210> SEQ ID NO 288
<211> LENGTH: 35
<212> TYPE: DNA
<213> ORGANISM: Artificial Sequence
<220> FEATURE:
```

<223> OTHER INFORMATION: Description of Artificial Sequence: Synthetic
       probe

<400> SEQUENCE: 288
aaggcttgta gatagtattg tttcatggtc caaag                              35

<210> SEQ ID NO 289
<211> LENGTH: 35
<212> TYPE: DNA
<213> ORGANISM: Artificial Sequence
<220> FEATURE:
<223> OTHER INFORMATION: Description of Artificial Sequence: Synthetic
       probe

<400> SEQUENCE: 289
aaggcttgta gatagtattg tttcatggtc caaag                              35

<210> SEQ ID NO 290
<211> LENGTH: 18
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 290
gcattctgac tcctgggt                                                 18

<210> SEQ ID NO 291
<211> LENGTH: 18
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 291
gcattctgac tcctgggt                                                 18

<210> SEQ ID NO 292
<211> LENGTH: 18
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 292
gcattctgac tcctgggt                                                 18

<210> SEQ ID NO 293
<211> LENGTH: 25
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 293
gtcattacta ctgtacaagt tccat                                         25

<210> SEQ ID NO 294
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 294
gtcattacta ctgtacaagt tccat                                         25

<210> SEQ ID NO 295
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 295
gtcattacta ctgtacaagt tccat                                         25

<210> SEQ ID NO 296
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 296
gcattctgac tcctgggt                                                 18

<210> SEQ ID NO 297
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 297
gcattctgac tcctgggt                                                 18

<210> SEQ ID NO 298
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 298
gcattctgac tcctgggt                                                 18

<210> SEQ ID NO 299
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 299
gtcattacta ctgtacaagt tccat                                         25

<210> SEQ ID NO 300
<211> LENGTH: 25
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 300
gtcattacta ctgtacaagt tccat                                          25

<210> SEQ ID NO 301
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 301
gtcattacta ctgtacaagt tccat                                          25

<210> SEQ ID NO 302
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 302
gcattctgac tcctgggt                                                  18

<210> SEQ ID NO 303
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 303
gcattctgac tcctgggt                                                  18

<210> SEQ ID NO 304
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 304
gcattctgac tcctgggt                                                  18

<210> SEQ ID NO 305
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 305
caagttccat tgatacaaac gca                                            23

<210> SEQ ID NO 306
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 306
caagttccat tgatacaaac gca                                            23

<210> SEQ ID NO 307
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 307
caagttccat tgatacaaac gca                                            23

<210> SEQ ID NO 308
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 308
gtcattacta ctgtacaagt tccat                                          25

<210> SEQ ID NO 309
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 309
gtcattacta ctgtacaagt tccat                                          25

<210> SEQ ID NO 310
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 310
gtcattacta ctgtacaagt tccat                                          25

<210> SEQ ID NO 311
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 311
gtcattacta ctgtacaagt tccat                                          25

<210> SEQ ID NO 312
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 312
```
gtcattacta ctgtacaagt tccat                                          25

<210> SEQ ID NO 313
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 313
gtcattacta ctgtacaagt tccat                                          25

<210> SEQ ID NO 314
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 314
caagttccat tgatacaaac gca                                            23

<210> SEQ ID NO 315
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 315
caagttccat tgatacaaac gca                                            23

<210> SEQ ID NO 316
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 316
caagttccat tgatacaaac gca                                            23

<210> SEQ ID NO 317
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 317
gtcattacta ctgtacaagt tccat                                          25

<210> SEQ ID NO 318
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 318

-continued

```
gtcattacta ctgtacaagt tccat                                            25

<210> SEQ ID NO 319
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 319
gtcattacta ctgtacaagt tccat                                            25

<210> SEQ ID NO 320
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 320
gtcattacta ctgtacaagt tccat                                            25

<210> SEQ ID NO 321
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 321
gtcattacta ctgtacaagt tccat                                            25

<210> SEQ ID NO 322
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 322
gtcattacta ctgtacaagt tccat                                            25

<210> SEQ ID NO 323
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 323
gtcattacta ctgtacaagt tccat                                            25

<210> SEQ ID NO 324
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 324
gtcattacta ctgtacaagt tccat                                            25
```

```
<210> SEQ ID NO 325
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 325
gtcattacta ctgtacaagt tccat                                              25

<210> SEQ ID NO 326
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 326
gtcattacta ctgtacaagt tccat                                              25

<210> SEQ ID NO 327
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 327
gtcattacta ctgtacaagt tccat                                              25

<210> SEQ ID NO 328
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 328
gtcattacta ctgtacaagt tccat                                              25

<210> SEQ ID NO 329
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 329
gtcattacta ctgtacaagt tccat                                              25

<210> SEQ ID NO 330
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 330
gtcattacta ctgtacaagt tccat                                              25
```

```
<210> SEQ ID NO 331
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 331
gtcattacta ctgtacaagt tccat                                       25

<210> SEQ ID NO 332
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 332
gtcattacta ctgtacaagt tccat                                       25

<210> SEQ ID NO 333
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 333
gtcattacta ctgtacaagt tccat                                       25

<210> SEQ ID NO 334
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 334
gtcattacta ctgtacaagt tccat                                       25

<210> SEQ ID NO 335
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 335
gtcattacta ctgtacaagt tccat                                       25

<210> SEQ ID NO 336
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 336
gtcattacta ctgtacaagt tccat                                       25
```

```
<210> SEQ ID NO 337
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 337
gtcattacta ctgtacaagt tccat                                          25

<210> SEQ ID NO 338
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 338
gtcattacta ctgtacaagt tccat                                          25

<210> SEQ ID NO 339
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 339
gtcattacta ctgtacaagt tccat                                          25

<210> SEQ ID NO 340
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 340
gtcattacta ctgtacaagt tccat                                          25

<210> SEQ ID NO 341
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 341
gcattctgac tcctgggt                                                  18

<210> SEQ ID NO 342
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 342
tgcattctga ctcctgggt                                                 19

<210> SEQ ID NO 343
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 343
caagttccat tgatacaaac gca                                            23

<210> SEQ ID NO 344
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 344
tacaagttcc attgatacaa acgca                                          25

<210> SEQ ID NO 345
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 345
gtcattacta ctgtacaagt tccat                                          25

<210> SEQ ID NO 346
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 346
gcattctgac tcctgggt                                                  18

<210> SEQ ID NO 347
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 347
gcattctgac tcctgggt                                                  18

<210> SEQ ID NO 348
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 348
tgcattctga ctcctgggt                                                 19

<210> SEQ ID NO 349
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 349
tgcattctga ctcctgggt                                                19

<210> SEQ ID NO 350
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 350
gcattctgac tcctgggt                                                 18

<210> SEQ ID NO 351
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 351
tgcattctga ctcctgggt                                                19

<210> SEQ ID NO 352
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 352
caagttccat tgatacaaac gca                                           23

<210> SEQ ID NO 353
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 353
caagttccat tgatacaaac gca                                           23

<210> SEQ ID NO 354
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 354
caagttccat tgatacaaac gca                                           23

<210> SEQ ID NO 355
<211> LENGTH: 25
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 355
tacaagttcc attgatacaa acgca                                          25

<210> SEQ ID NO 356
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 356
tacaagttcc attgatacaa acgca                                          25

<210> SEQ ID NO 357
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 357
tacaagttcc attgatacaa acgca                                          25

<210> SEQ ID NO 358
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 358
gtcattacta ctgtacaagt tccat                                          25

<210> SEQ ID NO 359
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 359
gtcattacta ctgtacaagt tccat                                          25

<210> SEQ ID NO 360
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 360
gtcattacta ctgtacaagt tccat                                          25

<210> SEQ ID NO 361
<211> LENGTH: 18
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 361
accataatga ccgatggc                                                       18

<210> SEQ ID NO 362
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 362
cgcctcgtac aaaatcttca a                                                   21

<210> SEQ ID NO 363
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 363
attcctcata ataaaattg ggtg                                                 24

<210> SEQ ID NO 364
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 364
attcctcata atgaaaattg ggtg                                                24

<210> SEQ ID NO 365
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 365
ccagttgtcc ctgcatac                                                       18

<210> SEQ ID NO 366
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 366
aggtcgattt gaaccatgc                                                      19

<210> SEQ ID NO 367
<211> LENGTH: 10
<212> TYPE: DNA
<213> ORGANISM: Artificial Sequence
<220> FEATURE:
```

-continued

```
<223> OTHER INFORMATION: Description of Artificial Sequence: Synthetic
      oligonucleotide

<400> SEQUENCE: 367
aaacacgtgc                                                             10

<210> SEQ ID NO 368
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 368
ccttgttcca                                                             10

<210> SEQ ID NO 369
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 369
cagggacgat                                                             10
```

OPTIMIZED PROBES AND PRIMERS AND METHODS OF USING SAME FOR THE BINDING, DETECTION, DIFFERENTIATION, ISOLATION AND SEQUENCING OF INFLUENZA A; INFLUENZA B; NOVEL INFLUENZA A/H1N1; AND A NOVEL INFLUENZA A/H1N1 RNA SEQUENCE MUTATION ASSOCIATED WITH OSELTAMIVIR RESISTANCE

RELATED APPLICATIONS

This application claims the benefit of U.S. Provisional Application No. 61/244,435, filed on Sep. 21, 2009 and U.S. Provisional Application No. 61/251,616, filed on Oct. 14, 2009, the contents of which are incorporated by reference herein in their entirety.

SEQUENCE LISTING

The instant application contains a Sequence Listing which has been submitted in ASCII format via EFS-Web and is hereby incorporated by reference in its entirety. Said ASCII copy, created on May 26, 2011, is named 91080555.txt.

BACKGROUND

Influenza viruses are enveloped, single stranded negative-sense, segmented genome RNA viruses of the family Orthomyxoviridae. Influenza viruses are divided into three distinct types A, B and C; only types A and B have been identified as a concern in human pathogenicity.

Influenza A viruses are subtyped based upon antigenicity and genetics of their surface proteins, hemaglutinin (HA) and neuraminidase (NA), which are the major targets of the host organism's immune system. Contemporary circulating seasonal influenza A viruses are classified as H1N1 or H3N2. Influenza B viruses are mainly found in humans. All types of influenza have been shown to undergo antigenic shift and drift, though at different rates.

2009 influenza A/H1N1, also referred to as "swine flu" or 2009 influenza H1N1, is a new influenza virus that was first detected in humans in the United States and Mexico in April 2009. 2009 influenza A/H1N causes a range of influenza-like illness in humans, including cough, fever, sore throat, body aches and headache. The virus is highly contagious and spreads quickly.

Seasonal influenza strains (such as influenza A and influenza B) customarily peak in incidence and disease with a seasonal periodicity. Seasonal influenza currently circulating consists of influenza A/H1N1, influenza A/H3N2 and influenza B.

Certain strains of influenza are resistant to the antiviral drug oseltamivir (trade name Tamiflu®). For seasonal influenza A/H1N1, resistance is indicated by an RNA sequence mutation resulting in a CAT→TAT substitution that causes an amino acid change at position 275 (H275Y) in the neuraminidase protein. The change in the coding triplet from CAT to TAT is reflected by a change in the encoded amino acid. CAT normally encodes a histidine while the TAT coding triplet encodes a tyrosine. For 2009 influenza A/H1N1, resistance is also indicated by the same protein sequence mutation resulting in a histidine-to-tyrosine substitution at position 275 (H275Y) in the neuraminidase gene, but the RNA codon change is CAC→TAC.

In the United States, more than 200,000 people are hospitalized from influenza-related causes and an average of 36,000 people die from influenza-related complications annually. Transmission of the influenza virus occurs by aerosol, such as coughing and sneezing, and with contact with nasal discharge. Close contact and indoor environments favor transmission. Humans infected with seasonal and 2009 influenza A/H1N1 shed virus and may be able to infect others from 1 day before showing signs of illness to 5 to 7 days after becoming ill. The human influenza viruses are easily transmitted from human to human.

Symptoms of influenza A and B infections are characterized by fever, chills, anorexia, headache, myalgia, weakness, sneezing, rhinitis, sore throat and a nonproductive cough. In approximately half of all cases, nausea and vomiting may occur.

Traditional testing for influenza is performed using viral culture methods. Currently, the majority of influenza testing is performed using rapid lateral flow assays or rapid antigen detection assays, which are designed to either detect and discriminate influenza A and influenza B, or simply detect influenza A.

In the United States, four prescription antiviral medications, oseltamivir, zanamivir, amantadine and rimantadine, are approved for treatment and chemoprophylaxis of influenza. The majority of 2009 influenza A/H1N1 remains sensitive to oseltamivir and zanamivir but are resistant to amantadine and rimatadine, however, oseltamivir resistance has recently been identified in 2009 influenza A/H1N1 patient isolates. This, along with documented widespread oseltamivir resistance in seasonal influenza A/H1N1, presents challenges for the selection of antiviral medications for treatment and chemoprophylaxis of influenza.

Influenza detection and differentiation, in combination with identification of oseltamivir resistance in 2009 influenza A/H1N1 strains, would allow for improved treatments of viral infections. A rapid and accurate diagnostic test panel for the simultaneous detection and differentiation of influenza A, influenza B, and 2009 influenza A/H1N1 and the determination if the mutation for oseltamivir resistance is present in samples positive for 2009 A/H1N1, therefore, would provide clinicians with an effective tool for identifying patients symptomatic for one or more of the influenza viruses and subsequently supporting effective treatment regimens.

SUMMARY

The present invention is directed to detect the presence of influenza virus (influenza A, influenza B and 2009 influenza A/H1N1), distinguishing 2009 influenza A/H1N1 (also referred to as Swine-origin influenza Virus (S-oIV) pandemic 2009 strain or "swine flu") from seasonal flu, and determining if the mutation for oseltamivir resistance is present in samples positive for 2009 influenza A/H1N1.

Described herein are nucleic acid probes and primers for binding, detecting, discriminating, isolating and sequencing all known, characterized variants of influenza A, influenza B and 2009 influenza A/H1N1, with a high degree of sensitivity and specificity. Also described herein are nucleic acid probes and primers for detecting, discriminating, isolating and sequencing influenza A and 2009 influenza A/H1N1. Also described herein are nucleic acid probes and primers for detecting, discriminating, isolating and sequencing 2009 influenza A/H1N1 and 2009 influenza A/H1N1 resistance and/or sensitivity to oseltamivir. These primers and probes can detect influenza nucleic acids containing the CAC influenza RNA sequence coding for histidine at amino acid position 275 in the neuraminidase gene of 2009 influenza A/H1N1, from influenza nucleic acids containing the TAC RNA sequence coding for tyrosine, implicated in influenza resistance to oseltamivir (trade name is Tamiflu®). All of the above described assays also include a process control.

A diagnostic test or tests that distinguish influenza A, influenza B and 2009 influenza A/H1N1 simultaneously, or that distinguishes influenza A and 2009 influenza A/H1N1, and/or that distinguishes 2009 influenza A/H1N1 and oseltamivir resistance and/or sensitivity in humans are necessary because such detection is critical in early patient identification and treatment. The assays described herein also aid in the intervention of the spread of these highly infectious viruses.

The assays described herein are used to identify or confirm the identification of influenza A, influenza B and 2009 influenza A/H1N1, detect genetic mutations in 2009 influenza A/H1N1 inferred to confer resistance to oseltamivir and detect wild-type sequences that indicate sensitivity to oseltamivir. The assays may be performed in a single testing scheme consisting of simultaneous analysis of the same patient sample in two separate reactions. The first reaction may consist of, for example, the identification of influenza A, influenza B and 2009 influenza A/H1N1. The second reaction may consist of, for example, the identification of 2009 influenza A/H1N1 and the detection of genetic mutations in 2009 influenza A/H1N1 inferred to confer resistance to oseltamivir and/or the detection of wild-type sequences that indicate sensitivity to oseltamivir. Assay results for all tests may be delivered simultaneously. The reaction containing the 2009 influenza A/H1N1 and oseltamivir resistance or sensitivity information could also be performed alone, on samples previously testing positive for "nonsubtypeable H1N1".

Alternatively, the assays can be performed in a single testing scheme consisting of simultaneous analysis of the same patient sample in two separate reactions. The first reaction can be directed to, for example, the identification of influenza A and 2009 influenza A/H1N1. The second reaction can be directed to, for example, the identification of 2009 influenza A/H1N1 and the detection of genetic mutations in 2009 influenza A/H1N1 inferred to confer resistance to oseltamivir and/or the detection of wild-type sequences that indicate sensitivity to oseltamivir. Assay results for all tests can be obtained and/or delivered simultaneously.

The assays described herein furthermore include a diagnostic test that distinguishes seasonal H1N1 from H3N2 using resistance genotyping or distinguishes seasonal H1N1 from seasonal H3N2 by subtyping. Furthermore, the assays described herein can be combined into two reactions. The first reaction may consist of, for example, the identification of influenza A, influenza B and 2009 influenza A/H1N1. The second reaction may consist of, for example, detection of genetic mutations in 2009 influenza A/H1N1 inferred to confer resistance to oseltamivir and/or the detection of wild-type sequences that indicate sensitivity to oseltamivir, as well as seasonal H1N1 from H3N2 using resistance genotyping.

In addition, the assays described herein involve a first reaction which may consist of, for example, the identification of influenza A, influenza B and 2009 influenza A/H1N1. The second reaction may consist of, for example, distinguishing seasonal H1N1 from seasonal H3N2 by subtyping.

Many facilities utilize viral culture-based methods for the determination and detection of influenza infections, which requires days to obtain the results. The methods of detection of the present invention described herein occurs within a minimal number of hours, allowing clinicians to rapidly determine the appropriate treatment options for individuals infected with influenza virus(es).

One embodiment is directed to an isolated nucleic acid sequence comprising a sequence selected from the group consisting of: SEQ ID NOS: 1-366.

One embodiment is directed to a method of hybridizing one or more isolated nucleic acid sequences comprising a sequence selected from the group consisting of: SEQ ID NOS: 1-67 and 77-366 to an influenza A, influenza B and/or 2009 influenza A/H1N1 sequence and/or influenza A/H3N2 sequence, comprising contacting one or more isolated nucleic acid sequences to a sample comprising the influenza sequence under conditions suitable for hybridization. In a particular embodiment, the sequence is a genomic sequence, a naturally occurring plasmid, a naturally occurring transposable element, a template sequence or a sequence derived from an artificial construct. In a particular embodiment, the method(s) further comprise isolating and/or sequencing the hybridized influenza sequence.

One embodiment is directed to a primer set comprising at least one forward primer selected from the group consisting of SEQ ID NOS: 1, 4, 7, 11, 13, 14, 19, 24, 27, 30, 33, 36, 39, 42, 45, 48, 51, 52, 53, 57, 61, 68, 71 and 74; and at least one reverse primer selected from the group consisting of SEQ ID NOS: 3, 6, 9, 10, 12, 16, 18, 21, 23, 26, 28, 29, 32, 34, 35, 38, 41, 44, 47, 50, 55, 59, 62, 70, 73 and 76.

One embodiment is directed to a primer set comprising at least one forward primer selected from the group consisting of SEQ ID NOS: 77-100, 148-218, 361 and 362; and at least one reverse primer selected from the group consisting of SEQ ID NOS: 124-147, 290-360, 365 and 366.

One embodiment is directed to a primer set (at least one forward primer and at least one reverse primer) selected from the group consisting of: Groups 1-116 of Table 4.

One embodiment is directed to a method of producing a nucleic acid product, comprising contacting one or more isolated nucleic acid sequences selected from the group consisting of SEQ ID NOS: 1, 3, 4, 6, 7, 9, 10-14, 16, 18, 19, 21, 23, 24, 26-30, 32-36, 38-39, 41, 42, 44, 45, 47, 48, 50-53, 55, 57, 59, 61, 62, 68, 70, 71, 73, 74 and 76 to a sample comprising an influenza sequence under conditions suitable for nucleic acid polymerization. In a particular embodiment, the nucleic acid product is an influenza amplicon produced using at least one forward primer selected from the group consisting of SEQ ID NOS: 1, 4, 7, 11, 13, 14, 19, 24, 27, 30, 33, 36, 39, 42, 45, 48, 51, 52, 53, 57 and 61 and at least one reverse primer selected from the group consisting of SEQ ID NOS: 3, 6, 9, 10, 12, 16, 18, 21, 23, 26, 28, 29, 32, 34, 35, 38, 41, 44, 47, 50, 55, 59 and 62.

One embodiment is directed to a probe that hybridizes to an amplicon produced as described herein, e.g., using the primers described herein. In a particular embodiment, the probe comprises a sequence selected from the group consisting of SEQ ID NOS: 2, 5, 8, 15, 17, 20, 22, 25, 31, 37, 40, 43, 46, 49, 54, 56, 58, 60, 63-67, 69, 72, 75, 101-123, 219-289, 363 and 364. In a particular embodiment, the probe(s) is labeled with a detectable label selected from the group consisting of: a fluorescent label, a chemiluminescent label, a quencher, a radioactive label, biotin and gold.

One embodiment is directed to a set of probes that hybridize to an amplicon produced as described herein, e.g., using the primers described herein. In a particular embodiment, a first probe can comprise an influenza A sequence, for example, selected from the group consisting of SEQ ID NO: 2; a second probe can comprise an influenza B sequence, for example, selected from the group consisting of SEQ ID NOS: 5, 8, 15, 17, 20, 22 and 25; a third probe can comprise a 2009 influenza A/H1N1 sequence, for example, SEQ ID NOS: 31, 37, 40, 43 and 46; and a fourth probe can comprise a process control sequence, for example, selected from the group consisting of SEQ ID NOS: 69, 72 and 75. In another embodiment, a first probe comprises an influenza A probe, for example, SEQ ID NO: 2; a second probe comprises a 2009 influenza A/H1N1 probe, for example, SEQ ID NOS: 31, 37, 40, 43 and 46; and a third probe comprises a process control probe sequence, for example, selected from the group consisting of SEQ ID NOS: 69, 72 and 75. In another embodiment, a first probe comprises a 2009 influenza A/H1N1 probe, for example, SEQ ID NOS: 31, 37, 40, 43 and 46; a second probe comprises an oseltamivir-resistance marker sequence, for example, selected from the group consisting of SEQ ID NOS: 56, 58, 63, 64, 67; a third probe comprises an oseltamivir-sensitive marker sequence, for example, selected from the group consisting of: SEQ ID NOS: 49, 54, 60, 65 and 66; and a fourth probe comprises a process control sequence selected from the group consisting of SEQ ID NOS: 69, 72 and 75. In a particular embodiment, each of the probes is labeled with a different detectable label. In additional embodiments, one or more of the probes is labeled with the same detectable label.

In an additional embodiment, a first probe comprises an influenza A sequence, for example, SEQ ID NO: 2; a second probe comprises a 2009 influenza A/H1N1 sequence, for example, SEQ ID NOS: 31, 37, 40, 43 and 46; a third probe comprises an oseltamivir resistance or sensitive marker sequence, for example, selected from the group consisting of SEQ ID NOS: 49, 54, 56, 58, 60 and 63-67; and a fourth probe comprises a process control sequence, for example, selected from the group consisting of SEQ ID NOS: 69, 72 and 75. In a particular embodiment, each of the probes is labeled with a different detectable label. In a particular embodiment, the first probe and the second probe are labeled with the same detectable label.

One embodiment is directed to a probe that hybridizes directly to the genomic sequences of the target without amplification. In a particular embodiment, the probe comprises a sequence, for example, selected from the group consisting of SEQ ID NOS: 2, 5, 8, 15, 17, 20, 22, 25, 31, 37, 40, 43, 46, 49, 54, 56, 58, 60, 63-67, 69, 72 and 75. In a particular embodiment, the probe(s) is labeled with a detectable label, for example, selected from the group consisting of: a fluorescent label, a chemiluminescent label, a quencher, a radioactive label, biotin and gold.

One embodiment, using any of the probe combinations described herein, is directed to a set of probes that hybridize directly to the genomic sequences of the target without amplification.

In one embodiment, the probe(s) is fluorescently labeled and the step of detecting the binding of the probe to the amplified product comprises measuring the fluorescence of the sample. In one embodiment, the probe comprises a fluorescent reporter moiety and a quencher of fluorescence-quenching moiety. Upon probe hybridization with the amplified product, the exonuclease activity of a DNA polymerase dissociates the probe's fluorescent reporter and the quencher, resulting in the unquenched emission of fluorescence, which is detected. An increase in the amplified product causes a proportional increase in fluorescence, due to cleavage of the probe and release of the reporter moiety of the probe. The amplified product is quantified in real time as it accumulates. In another embodiment, each probe in the multiplex reaction is labeled with a different distinguishable and detectable label.

In a particular embodiment, the probes are molecular beacons. Molecular beacons are single-stranded probes that form a stem-and-loop structure. A fluorophore is covalently linked to one end of the stem and a quencher is covalently linked to the other end of the stem forming a stem hybrid; fluorescence is quenched when the formation of the stem loop positions the fluorophore proximal to the quencher. When a molecular beacon hybridizes to a target nucleic acid sequence, the probe undergoes a conformational change that results in the dissociation of the stem hybrid and, thus the fluorophore and the quencher move away from each other, enabling the probe to fluoresce brightly. Molecular beacons can be labeled with differently colored fluorophores to detect different target sequences. Any of the probes described herein may be designed and utilized as molecular beacons. In a particular embodiment, the probe to detect resistance to oseltamivir and the probe to detect sensitivity to oseltamivir are molecular beacons. In a particular embodiment, each of these probes is labeled with a different label. The preferred format for detection of oseltamivir sensitivity uses two probes, one that will hybridize to viral strains that are sensitive to oseltamivir and a second that will hybridize to viral strains that contain the 2009 H1N1-specific H275Y mutation. In this format, a positive signal is produced for oseltamivir status, whether the strain is sensitive or resistant.

Four strategies are employed in the design of probes to discriminate between sensitive and resistant phenotypes. The first strategy uses nucleic acid modification technologies (Minor Groove Binder (MGB) or BHQ-plus) that can both stabilize the probe-target hybrid and contribute to the discriminatory properties of the probe. The second approach uses molecular beacons (described above) that also have enhanced discriminatory properties. The third strategy employs locked nucleic acid (LNA) technology that also stabilizes the probe-target hybrid and has enhanced discriminatory properties. The fourth strategy uses TaqMan® probe technology. With any of the strategies described herein, the probes for oseltamivir-sensitivity and oseltamivir-resistance will be labeled with different dyes, to allow simultaneous detection.

One embodiment is directed to a method for detecting influenza A, influenza B and/or 2009 influenza A/H1N1 DNA and/or resistance or sensitivity to oseltamivir in 2009 influenza A/H1N1 in a sample, comprising: (a) contacting the sample with at least one forward primer comprising a sequence selected from the group consisting of: SEQ ID NOS: 1 (influenza A); 4, 7, 11, 13, 14, 19, 24, 27 (influenza B); 30, 33, 36, 39, 42, 45 (2009 influenza A/H1N1); and 48, 51-53, 57, 61 (oseltamivir resistance/sensitive marker), and at least one reverse primer comprising a sequence selected from the group consisting of: SEQ ID NO: 3 (influenza A); 6, 9, 10, 12, 16, 18, 21, 23, 26, 28, 29 (influenza B); 32, 34, 35, 38, 41, 44, 47 (2009 influenza A/H1N1); and 50, 55, 59 and 62 (oseltamivir resistance and sensitive markers), under conditions such that nucleic acid amplification occurs to yield an amplicon; and (b) contacting the amplicon with one or more probes comprising one or more sequences selected from the group consisting of: SEQ ID NOS: 2 (influenza A); 5, 8, 15, 17, 20, 22, 25 (influenza B); 31, 37, 40, 43, 46 (2009 influenza A/H1N1); and 49, 54, 56, 58, 60, 63-67 (oseltamivir resistance or sensitive markers), under conditions such that hybridization of the probe to the amplicon occurs, wherein hybridization of the probe is indicative of influenza A, influenza B and/or 2009 influenza A/H1N1 DNA and/or resistance or sensitivity to oseltamivir in the sample.

One embodiment is directed to a method for detecting influenza A and/or 2009 influenza A/H1N1 DNA and/or resistance or sensitivity to oseltamivir in 2009 influenza A/H1N1 in a sample, comprising: (a) contacting the sample with at least one forward primer comprising a sequence selected from the group consisting of: SEQ ID NOS: 1 (influenza A);

4, 7, 11, 13, 14, 19, 24, 27 (influenza B); 30, 33, 36, 39, 42, 45 (2009 influenza A/H1N1); and 48, 51-53, 57, 61 (oseltamivir resistance/sensitive marker); and at least one reverse primer comprising a sequence selected from the group consisting of: SEQ ID NO: 3 (influenza A); 6, 9, 10, 12, 16, 18, 21, 23, 26, 28, 29 (influenza B); 32, 34, 35, 38, 41, 44, 47 (2009 influenza A/H1N1); and 50, 55, 59 and 62 (oseltamivir resistance and sensitive markers), under conditions such that nucleic acid amplification occurs to yield an amplicon; and (b) contacting the amplicon with one or more probes comprising one or more sequences selected from the group consisting of: SEQ ID NOS: 2 (influenza A); 5, 8, 15, 17, 20, 22, 25 (influenza B); 31, 37, 40, 43, 46 (2009 influenza A/H1N1); and 49, 54, 56, 58, 60, and 63-67 (oseltamivir resistance or sensitive markers), under conditions such that hybridization of the probe to the amplicon occurs, wherein hybridization of the probe is indicative of influenza A and/or 2009 influenza A/H1N1 DNA and/or resistance or sensitivity to oseltamivir in the sample.

In a particular embodiment, each of the one or more probes is labeled with a different detectable label. In a particular embodiment, the one or more probes are labeled with the same detectable label. In a particular embodiment, the sample is selected from the group consisting of: saliva, fluids collected from the ear, eye, mouth, and respiratory airways, sputum, tears, oropharyngeal swabs, nasopharyngeal swabs, throat swabs, nasopharyngeal aspirates, bronchoalveolar lavage fluid, skin swabs, nasal aspirates, nasal wash, and fluids and cells obtained by the perfusion of tissues of both human and animal origin. In one embodiment, the sample is from a human, is non-human in origin, or is derived from an inanimate object or environmental surfaces. In a particular embodiment, the at least one forward primer, the at least one reverse primer and the one or more probes are selected from the group consisting of: Groups 1-32 of Table 4. In a particular embodiment, the method(s) further comprise isolating and/or sequencing the influenza A, influenza B and/or 2009 influenza A/H1N1 DNA and/or genotyping the type of oseltamivir resistance.

One embodiment is directed to a primer set or collection of primer sets for amplifying DNA of an influenza A strain, comprising a nucleotide sequence selected from the group consisting of: SEQ ID NOS: 1 and 3.

One embodiment is directed to a primer set or collection of primer sets for amplifying DNA of an influenza B strain, comprising a nucleotide sequence selected from the group consisting of: (1) SEQ ID NOS: 4, 6, 7 and 9; (2) SEQ ID NOS: 4 and 9-11; (3) SEQ ID NOS: 4, 6, 9 and 11; (4) SEQ ID NOS: 4, 7, 9 and 10; (5) SEQ ID NOS: 4, 7, 9 and 12; (6) SEQ ID NOS: 7, 9, 10 and 13; (7) SEQ ID NOS: 14, 16 and 18; (8) SEQ ID NOS: 4, 7 and 9; (9) SEQ ID NOS: 19 and 21; (10) SEQ ID NOS: 19 and 23; (11) SEQ ID NOS: 24-28; and (12) SEQ ID NOS: 24, 26, 27 and 29.

One embodiment is directed to a primer set or collection of primer sets for amplifying DNA of a 2009 influenza A/H1N1 strain, comprising a nucleotide sequence selected from the group consisting of: (1) SEQ ID NOS: 30-34; (2) SEQ ID NOS: 30 and 33-35; (3) SEQ ID NOS: 36, 38, 39 and 41; and (4) SEQ ID NOS: 42, 44, 45 and 47.

One embodiment is directed to a primer set or collection of primer sets for amplifying DNA of a oseltamivir-resistant or sensitive 2009 influenza A/H1N1 strain, comprising a nucleotide sequence selected from the group consisting of: (1) SEQ ID NOS: 48, 50 and 51; (2) SEQ ID NOS: 48-52; (3) SEQ ID NOS: 50 and 52; (4) SEQ ID NOS: 53 and 55; (5) SEQ ID NOS: 57 and 59; and (6) SEQ ID NOS: 61 and 62.

One particular embodiment is directed to oligonucleotide probes for binding to DNA of influenza A and/or influenza B and/or 2009 influenza A/H1N1 and/or oseltamivir-resistant or -sensitive 2009 influenza A/H1N1, comprising a nucleotide sequence selected from the group consisting of: SEQ ID NOS: 2 (influenza A); 5, 8, 15, 17, 20, 22, 25 (influenza B); 31, 37, 40, 43, 46 (2009 influenza A/H1N1); and 49, 54, 56, 58, 60, 63-67 (oseltamivir resistant or sensitive marker).

One embodiment is directed to the simultaneous detection and differentiation in a multiplex format of (1) influenza A, and/or (2) influenza B, and/or (3) 2009 influenza A/H1N1.

One embodiment is directed to the simultaneous detection and differentiation in a multiplex format of (1) influenza A and (2) 2009 influenza A/H1N1.

One embodiment is directed to the simultaneous detection and differentiation in a multiplex format of (1) 2009 influenza A/H1N1; and/or (2) oseltamivir-resistant 2009 influenza A/H1N1; and/or (2) oseltamivir-sensitive 2009 influenza A/H1N1.

One embodiment is directed to the simultaneous detection and differentiation in a multiplex format of (1) influenza A; and/or (2) 2009 influenza A/H1N1; and/or (3) oseltamivir-resistant 2009 influenza A/H1N1 and/or (4) oseltamivir-sensitive 2009 influenza A/H1N1.

One embodiment is directed to a primer set or collection of primer sets for amplifying DNA of influenza A, and/or influenza B and/or 2009 influenza A/H1N1 simultaneously, comprising:

(a) SEQ ID NOS: 1 and 3 (forward and reverse primers for amplifying DNA of influenza A, respectively); and (b) (1) SEQ ID NOS: 4, 6, 7 and 9; (2) SEQ ID NOS: 4 and 9-11; (3) SEQ ID NOS: 4, 6, 9 and 11; (4) SEQ ID NOS: 4, 7, 9 and 10; (5) SEQ ID NOS: 4, 7, 9 and 12; (6) SEQ ID NOS: 7, 9, 10 and 13; (7) SEQ ID NOS: 14, 16 and 18; (8) SEQ ID NOS: 4, 7 and 9; (9) SEQ ID NOS: 19 and 21; (10) SEQ ID NOS: 19 and 23; (11) SEQ ID NOS: 24-28; and (12) SEQ ID NOS: 24, 26, 27 and 29 (forward and reverse primers for amplifying DNA of influenza B); and (c) (1) SEQ ID NOS: 30-34; (2) SEQ ID NOS: 30 and 33-35; (3) SEQ ID NOS: 36, 38, 39 and 41; and (4) SEQ ID NOS: 42, 44, 45 and 47 (forward and reverse primers for amplifying DNA of 2009 influenza A/H1N1).

A particular embodiment is directed to oligonucleotide probes for binding to DNA of influenza A, and/or influenza B and/or 2009 influenza A/H1N1, comprising a nucleotide sequence selected from the group consisting of SEQ ID NOS: 2 (influenza A probe); 5, 8, 15, 17, 20, 22, 25 (influenza B probes) and 31, 37, 40, 43, 46 (2009 influenza A/H1N1 probe).

One embodiment is directed to a primer set or collection of primer sets for amplifying DNA of influenza A and/or 2009 influenza A/H1N1 simultaneously, comprising:

(a) SEQ ID NOS: 1 and 3 (forward and reverse primers for amplifying DNA of influenza A, respectively); and (b) (1) SEQ ID NOS: 30-34; (2) SEQ ID NOS: 30 and 33-35; (3) SEQ ID NOS: 36, 38, 39 and 41; and (4) SEQ ID NOS: 42, 44, 45 and 47 (forward and reverse primers for amplifying DNA of 2009 influenza A/H1N1).

A particular embodiment is directed to oligonucleotide probes for binding to DNA of influenza A and/or 2009 influenza A/H1N1, comprising a nucleotide sequence selected from the group consisting of SEQ ID NOS: 2 (influenza A probe); 31, 37, 40, 43, 46 (2009 influenza A/H1N1 probe).

One embodiment is directed to a primer set or collection of primer sets for amplifying DNA of 2009 influenza A/H1N1, oseltamivir-resistant 2009 influenza A/H1N1 and/or oseltamivir-sensitive 2009 influenza A/H1N1 simultaneously, comprising:

(a) (1) SEQ ID NOS: 30-34; (2) SEQ ID NOS: 30 and 33-35; (3) SEQ ID NOS: 36, 38, 39 and 41; and (4) SEQ ID NOS: 42, 44, 45 and 47 (forward and reverse primer pairs for amplifying DNA of 2009 influenza A/H1N1); and (b) (1) SEQ ID NOS: 48, 50 and 51; (2) SEQ ID NOS: 48-52; (3) SEQ ID NOS: 50 and 52; (4) SEQ ID NOS: 53 and 55; (5) SEQ ID NOS: 57 and 59; and (6) SEQ ID NOS: 61 and 62 (forward and reverse primers or primer pairs for amplifying DNA of oseltamivir-resistant or sensitive 2009 influenza A/H1N1).

A particular embodiment is directed to oligonucleotide probes for binding to DNA of 2009 influenza A/H1N1, oseltamivir-resistant 2009 influenza A/H1N1 and/or oseltamivir-sensitive 2009 influenza A/H1N1, comprising a nucleotide sequence selected from the group consisting of SEQ ID NOS: 31, 37, 40, 43, 46 (2009 influenza A/H1N1 probe); 49, 54, 56, 58, 60, and 63-67 (oseltamivir-resistant or sensitive 2009 influenza A/H1N1 probes).

One embodiment is directed to a primer set or collection of primer sets for amplifying DNA of influenza A, 2009 influenza A/H1N1, and/or oseltamivir-resistant 2009 influenza A/H1N1 and/or oseltamivir-sensitive 2009 influenza A/H1N1 simultaneously, comprising:

(a) (1) SEQ ID NOS: 1 and 3 (forward and reverse primers for amplifying DNA of influenza A, respectively); and (b) 1) SEQ ID NOS: 30-34; (2) SEQ ID NOS: 30 and 33-35; (3) SEQ ID NOS: 36, 38, 39 and 41; and (4) SEQ ID NOS: 42, 44, 45 and 47 (forward and reverse primer pairs for amplifying DNA of 2009 influenza A/H1N1); and (c) (1) SEQ ID NOS: 48, 50 and 51; (2) SEQ ID NOS: 48-52; (3) SEQ ID NOS: 50 and 52; (4) SEQ ID NOS: 53 and 55; (5) SEQ ID NOS: 57 and 59; and (6) SEQ ID NOS: 61 and 62 (forward and reverse primers or primer pairs for amplifying DNA of oseltamivir-resistant or sensitive 2009 influenza A/H1N1).

A particular embodiment is directed to oligonucleotide probes for binding to DNA of 2009 influenza A/H1N1, oseltamivir-resistant 2009 influenza A/H1N1 and/or oseltamivir-sensitive 2009 influenza A/H1N1, comprising a nucleotide sequence selected from the group consisting of SEQ ID NOS: 2 (influenza A); 31, 37, 40, 43, 46 (2009 influenza A/H1N1); and 49, 54, 56, 58, 60, 63-67 (oseltamivir resistant or sensitive 2009 influenza A/H1N1 probes and 69, 72 and 75 (Process Control).

One embodiment is directed to a kit for detecting DNA of an influenza virus in a sample, comprising one or more probes comprising a sequence selected from the group consisting of: SEQ ID NO: 2 (influenza A); 5, 8, 15, 17, 20, 22, 25 (influenza B); 31, 37, 40, 43, 46 (2009 influenza A/H1N1); 49, 54, 56, 58, 60, and 63-67 (oseltamivir resistant or sensitive 2009 influenza A/H1N1 probes) and 69, 72 and 75 (Process Control). In a particular embodiment, the kit further comprises a) at least one forward primer comprising the sequence selected from the group consisting of: SEQ ID NOS: 1 (influenza A); 4, 7, 11, 13, 14, 19, 24, 27 (influenza B); 30, 33, 36, 39, 42, 45 (2009 influenza A/H1N1); 48, 51-53, 57, 61 (oseltamivir resistance/sensitive marker); 68, 71 and 74 (Process Control); and b) at least one reverse primer comprising the sequence selected from the group consisting of: SEQ ID NOS: SEQ ID NO: 3 (influenza A); 6, 9, 10, 12, 16, 18, 21, 23, 26, 28, 29 (influenza B); 32, 34, 35, 38, 41, 44, 47 (2009 influenza A/H1N1); 50, 55, 59 and 62 (oseltamivir resistance and sensitive markers); and 70, 73, 76 (Process Control). In a particular embodiment, the kit further comprises reagents for isolating and/or sequencing the DNA in the sample. In a particular embodiment, the one or more probes are labeled with different detectable labels. In a particular embodiment, the one or more probes are labeled with the same detectable labels. In a particular embodiment, the at least one forward primer, the at least one reverse primer and the one or more probes are selected from the group consisting of: Groups 1-32 of Table 4.

One embodiment is directed to a method for diagnosing a condition, syndrome or disease in a human associated with an influenza virus, comprising: a) contacting a sample with at least one forward and reverse primer set selected from the group consisting of: Groups 1-29 of Table 4; b) conducting an amplification reaction, thereby producing an amplicon; and c) detecting the amplicon using one or more probes selected from the group consisting of: SEQ ID NOS: 2 (influenza A); 5, 8, 15, 17, 20, 22, 25 (influenza B); 31, 37, 40, 43, 46 (2009 influenza A/H1N1); and 49, 54, 56, 58, 60, 63-67 (oseltamivir resistance or sensitive markers); wherein the generation of an amplicon is indicative of the presence of an influenza virus in the sample. In a particular embodiment, the sample is saliva, fluids collected from the ear, eye, mouth, and respiratory airways, sputum, tears, oropharyngeal swabs, nasopharyngeal swabs, throat swabs, nasopharyngeal aspirates, bronchoalveolar lavage fluid, skin swabs, nasal aspirates, nasal wash, and fluids and cells obtained by the perfusion of tissues of both human and animal origin. In one embodiment, the sample is from a human, is non-human in origin, or is derived from an inanimate object or environmental surfaces. A sample may be collected from more than one collection site, e.g., oropharyngeal and nasopharyngeal swabs. In a particular embodiment, the complications, conditions, syndromes or diseases in humans associated with an influenza virus are selected from the group consisting of: fever, chills, anorexia, headache, myalgia, weakness, sneezing, rhinitis, sore throat, a nonproductive cough, nausea, vomiting, pneumonia and death.

One embodiment is directed to a kit for amplifying and sequencing DNA of an influenza virus in a sample, comprising: a) at least one forward primer or primer pair comprising the sequence selected from the group consisting of: SEQ ID NOS: 1 (influenza A); 4, 7, 11, 13, 14, 19, 24, 27 (influenza B); 30, 33, 36, 39, 42, 45 (2009 influenza A/H1N1); 48, 51-53, 57, 61 (oseltamivir resistance/sensitive marker); and b) at least one reverse primer or primer pair comprising the sequence selected from the group consisting of: SEQ ID NOS: 3 (influenza A); 6, 9, 10, 12, 16, 18, 21, 23, 26, 28, 29 (influenza B); 32, 34, 35, 38, 41, 44, 47 (2009 influenza A/H1N1); 50, 55, 59 and 62 (oseltamivir resistance and sensitive markers); and c) reagents for the sequencing of amplified DNA fragments.

One embodiment is directed to a process control target sequence (MS2 bacteriophage, GI:15081). The MS2 bacteriophage is a well-characterized single-stranded RNA (ssRNA) virus of the Leviviridae family that is known to infect Enterobacteria, but does not occur naturally in clinical sample types for which this assay is intended. This process control is detected by a forward primer (SEQ ID NO: 68, 71 or 74), a reverse primer (SEQ ID NO: 70, 73 or 76) and a probe (SEQ ID NO: 69, 72 or 75). The process control is added directly to the clinical sample to monitor the integrity of both nucleic acid extraction/purification and PCR amplification steps.

The positive control plasmids contain partial sequences for one or more of the targets (i.e., Influenza A, Influenza B, 2009 Influenza A/H1N1) and are used for in vitro transcription of target ssRNA for the assays. The positive control plasmids for each given target comprise a T7 promoter sequence upstream of a region between 200-400 nucleotides in length containing the sequences targeted by the forward primer, probe and reverse primer. The positive control plasmids are intended to be used as a control to confirm that the assays are performing within specifications.

The oligonucleotides of the present invention and their resulting amplicons do not cross react and, thus, will work together without negatively impacting each other. The primers and probes to detect influenza A, influenza B and 2009 influenza A/H1N1 do not cross react with each other. The primers and probes to detect oseltamivir-resistant 2009 influenza A/H1N1 or oseltamivir-sensitive 2009 influenza A/H1N1 do not cross react with the primers and probes to detect influenza A, influenza B and 2009 influenza A/H1N1. The primers and probes of the present invention do not cross react with other potentially contaminating species that would be present in a sample matrix.

DETAILED DESCRIPTION

A diagnostic test or tests that can simultaneously detect and differentiate influenza A, influenza B and 2009 influenza A/H1N1, distinguish 2009 influenza A/H1N1 from seasonal influenza, and determine if the mutation for oseltamivir resistance is present in samples positive for 2009 influenza A/H1N1 is necessary, as influenza infections are a primary health concern world-wide. Currently, a pandemic of 2009 influenza A/H1N1 is underway.

Described herein are optimized probes and primers that, alone or in various combinations, allow for the amplification, detection, differentiation, isolation, and sequencing of influenza viruses that can be found in clinical isolates. Specific probes and primers, i.e., probes and primers that detect all known and characterized strains of influenza A, influenza B, and 2009 influenza A/H1N1, have been discovered and are described herein. Nucleic acid primers and probes for detecting specific influenza genetic material and oseltamivir-resistance or sensitivity and methods for designing and optimizing the respective primer and probe sequences are described herein.

The primers and probes described herein can be used, for example, to identify and/or confirm symptomatic patients for the presence of influenza and/or to confirm suspected cases of oseltamivir-resistance, e.g., in clinical isolates, in a multiplex format.

The primers and probes of the present invention can be used for the detection of influenza A, and/or influenza B and/or 2009 influenza A/H1N1 DNA and/or oseltamivir-resistant or oseltamivir-sensitive 2009 influenza A/H1N1, without loss of assay precision or sensitivity. Currently, the detection of influenza strains and oseltamivir-resistance are tested separately; however, the multiplex format options of the present invention allow quick identification of strain speciation and resistance simultaneously.

Influenza A and B

Influenza is a respiratory illness caused by influenza A or B viruses that occurs in outbreaks and epidemics worldwide. Influenza A viruses undergo periodic changes in the antigenic characteristics of their envelope glycoproteins, the hemagglutinin and the neuraminidase. Changes in these glycoproteins are referred to as antigenic shifts, which are associated with epidemics and pandemics of influenza A. There are three major subtypes of hemagglutinins (H1, H2, and H3) and two subtypes of neuraminidases (N1 and N2) among influenza A viruses that infect humans. There are two subtypes of influenza A, H1N1 or H3N2. Influenza B viruses are less likely to undergo antigenic changes. (Dolin, R. influenza. In: Harrison's Principles of Process Medicine, 15th ed, Braunwald, E, Fauci, A S, Kasper, D L, et al. (Eds), McGraw Hill, New York, 2001, p. 1125). Influenza A outbreaks are usually seasonal and almost always occur during the winter months in the northern and southern hemispheres (which occur at different times of the year).

Symptoms of influenza include fever, headache, sore throat, myalgia, and weakness. Infection of influenza can be transmitted through sneezing and coughing via droplets and by contacting an animate or inanimate object that has flu virus on it. (Fiore A E; Shay D K; Broder K; Iskander J K; Uyeki T M; Mootrey G; Bresee J S; Cox N S, Prevention and Control of influenza: Recommendations of the Advisory Committee on Immunization Practices (ACIP), MMWR Recomm Rep. 2008 Aug. 8; 57(RR-7):1-60; Blachere F M; Lindsley W G; Pearce T A; Anderson S E; Fisher M; Khakoo R; Meade B J; Lander O; Davis S; Thewlis R E; Celik I; Chen B T; Beezhold D H, Measurement of Airborne influenza Virus in a Hospital Emergency Department, Clin Infect Dis. 2009 Jan 9). Influenza virus shedding increases one-half to one day following exposure, peaking on the second day, then rapidly declining. The average duration of shedding is 4 to 5 days. Children, elderly adults, immunocompromised hosts and patients with chronic illnesses can shed the virus for longer periods of time. (Carrat F; Vergu E; Ferguson N M; Lemaitre M; Cauchemez S; Leach S; Valleron A J, Time lines of infection and disease in human influenza: a review of volunteer challenge studies, Am J. Epidemiol. 2008 Apr. 1; 167(7):775-85. Epub 2008 Jan 29; Leekha S; Zitterkopf N L; Espy M J; Smith T F; Thompson R L; Sampathkumar P, Duration of influenza A virus shedding in hospitalized patients and implications for infection control, Infect Control Hosp Epidemiol. 2007 September; 28(9):1071-6).

Influenza infections may also have other presentations, such as afebrile respiratory illnesses. Complications of influenza include pneumonia, myositis and rhabdomyolysis, myalgias, central nervous system disease (CNS) including encephalitis, transverse myelitis, aseptic meningitis, and Guillain-Barré syndrome (GBS). (Bayer, WH. influenza B encephalitis. West J Med 1987; 147:466; Fujimoto S; Kobayashi M; Uemura 0; Iwasa M; Ando T; Katoh T; Nakamura C; Maki N; Togari H; Wada Y, PCR on cerebrospinal fluid to show influenza-associated acute encephalopathy or encephalitis, Lancet 1998 Sep. 12; 352(9131):873-5).

Two classes of antiviral drugs are available for the prevention and treatment of seasonal influenza, the neuraminidase inhibitors (zanamivir and oseltamivir) that are active against both influenza A and B and the adamantanes (amantadine and rimantadine) that are only active against influenza A. Oseltamivir or zanamivir is usually prescribed for targeted populations with exposure to patients with H3N2 influenza A, influenza B, or 2009 influenza A/H1N1. Zanamivir is usually the drug of choice during outbreaks that are suspected to be the result of oseltamivir-resistant influenza. (Fiore A. et al., Prevention and Control of influenza: Recommendations of the Advisory Committee on Immunization Practices (ACIP), MMWR Recomm Rep., 57(RR-7):1-60, 2008; Ong A. et al., J. Infect. Dis., 196:181-90, 2007).

2009 Influenza A/H1N1

In late March and early April 2009, an outbreak of 2009 influenza A/H1N1 virus infection was detected in Mexico, and soon afterwards in the United States. 2009 influenza A/H1N1 is a virus that represents a quadruple reassortment of two swine strains, one human strain, and one avian strain of influenza.

Symptoms of 2009 influenza A/H1N1 include fever (temperature of 100° F. or greater) with a cough or sore throat.

(United States Centers for Disease Control and Prevention. Interim guidance for clinicians on identifying and caring for patients with swine-origin influenza A (H1N1) virus infection available on-line http://www.cdc.gov/swineflu/identifyingpatients.htm). High risk groups for the development of 2009 influenza A/H1N1 infection are similar to those for seasonal influenza (children younger than 5 years old, adults older than 65 years old, pregnant women, and immunocompromised individuals).

The majority of strains of pandemic 2009 influenza A/H1N1 appears sensitive to the neuraminidase inhibitors, oseltamivir and zanamivir, but all strains have been resistant to amantadine and rimantadine. According to the World Health Organization, there are increasing reports of strains resistant to oseltamivir.

Oseltamivir Resistance

The present invention detects oseltamivir resistance in 2009 influenza A/H1N1.

In seasonal influenza A/H1N1, oseltamivir resistance is indicated by an RNA sequence mutation resulting in a CAT→TAT substitution at position 275 (H275Y) in the neuraminidase gene. In 2009 influenza A/H1N1, oseltamivir resistance is also indicated by an RNA sequence mutation resulting in a histidine-to-tyrosine substitution at position 275 (H275Y) in the neuraminidase gene, but the resulting codon change is CAC→TAC.

Oseltamivir resistance should be suspected following likely exposure to patients with seasonal 2009 influenza A/H1N1. Because oseltamivir-resistant H1N1 viruses may be susceptible to adamantanes, rimantadine can be used when zanamivir is contraindicated. This information is summarized, for example, by health advisories issued by the Centers for Disease Control (found, for example, at their world wide web site, www2a.cdc.gov/HAN/ArchiveSysNiewMsgV.asp?AlertNum=00279).

Assays

Tables 1 and 2 demonstrate various possible diagnostic outcome scenarios using the probes and primers described herein in diagnostic methods.

TABLE 1

| Target | Expected Results | | | | | Potential Results (Not Expected) |
|---|---|---|---|---|---|---|
| Inf. A | + | + | + | − | + | − |
| Inf. B | + | + | − | − | − | + |
| SW (H1N1) | + | − | − | − | + | + |
| MS2 (PC) | +/− | +/− | +/− | + | +/− | +/− |
| Interpretation | Inf. A/Inf. B/H1N1 | Inf. A and Inf. B | Inf. A | None | H1N1 | Inf. B/H1N1 |

+, target detected;
−, target not detected;
Inf. A corresponding to the influenza A strain;
Inf. B corresponding to the influenza B strain;
SW (H1N1) corresponding to the H1N1 strain;
MS2 (PC) corresponding to the process control.

TABLE 2

| Target | Expected Results | | | | | Potential Results (Not Expected) |
|---|---|---|---|---|---|---|
| SW (H1N1) | + | + | − | + | + | − |
| MT (resistant) | + | − | − | + | − | + |
| WT (sensitive) | − | + | − | + | − | + |
| MS2 (PC) | +/− | +/− | + | +/− | +/− | +/− |
| Interpretation | H1N1 and MT+ | H1N1 and WT+ | None | H1N1 with mixed MT+ and WT+ sample | H1N1 | None |

+, target detected;
−, target not detected;
SW corresponding to the H1N1 strain;
MT corresponding to strain with oseltamivir-resistance;
WT corresponding to wild-type strain with oseltamivir-sensitivity;
MS2 (PC) corresponding to the process control.

Detection of the process control (PC) indicates that the sample result is valid, where an absence of a signal corresponding to the PC indicates either an invalid result or that one or more of the specific targets is at a high starting concentration. A signal indicating a high starting concentration of specific target in the absence of a process control signal is considered to be a valid sample result.

The advantages of a multiplex format are: (1) simplified and improved testing and analysis; (2) increased efficiency and cost-effectiveness; (3) decreased turnaround time (increased speed of reporting results); (4) increased productivity (less equipment time needed); and (5) coordination/standardization of results for patients for multiple organisms (reduces error from inter-assay variation).

Detection of influenza and identification of whether a 2009 influenza A/H1N1 strain is oseltamivir-resistant or sensitive can lead to earlier and more effective treatment of a subject. The methods for diagnosing and detecting influenza and identification of resistance described herein can be coupled with effective treatment therapies (e.g., antivirals). The treatments for such infections will depend upon the clinical disease state of the patient, as determinable by one of skill in the art.

The present invention therefore provides a method for specifically detecting in a sample the presence of three influenza types and determining whether a 2009 influenza A/H1N1 strain is oseltamivir resistant or sensitive using the primers and probes provided herein. Of particular interest in this regard is the ability of the disclosed primers and probes, as well as those that can be designed according to the disclosed methods, to specifically detect all or a majority of presently characterized strains of known, characterized influenza variants. The optimized primers and probes are useful, therefore, for identifying and diagnosing influenza infection, whereupon an appropriate treatment can then be administered to the individual to eradicate the virus(es).

The present invention provides one or more sets of primers that can anneal to all currently identified influenza A, influenza B and 2009 influenza A/H1N1 strains and thereby amplify a target from a biological sample. The present invention provides, for example, at least a first primer and at least a second primer for influenza A, influenza B and 2009 influenza A/H1N1 and at least a first primer and at least a second primer for detection of oseltamivir resistance and sensitivity in 2009 influenza A/H1N1, each of which comprises a nucleotide sequence designed according to the inventive principles disclosed herein, which are used together to amplify DNA from influenza in a mixed-flora sample in a multiplex assay.

Also provided herein are probes that hybridize to the influenza sequences and/or amplified products derived from the influenza sequences. A probe can be labeled, for example, such that when it binds to an amplified or unamplified target sequence, or after it has been cleaved after binding, a fluorescent signal is emitted that is detectable under various spectroscopy and light measuring apparatuses. The use of a labeled probe, therefore, can enhance the sensitivity of detection of a target in an amplification reaction of DNA of influenza because it permits the detection of viral-derived DNA at low template concentrations that might not be conducive to visual detection as a gel-stained amplification product.

Primers and probes are sequences that anneal to a viral genomic or viral genomic derived sequence, e.g., the influenza strains (the "target" sequence). The target sequence can be, for example, an anti-viral resistance mutation or a viral genome. In one embodiment, the entire gene sequence can be "scanned" for optimized primers and probes useful for detecting the anti-viral resistance mutation or the viral genome. In other embodiments, particular regions of the genome can be scanned, e.g., regions that are documented in the literature as being useful for detecting multiple genes, regions that are conserved, or regions where sufficient information is available in, for example, a public database, with respect to the antibiotic resistance genes.

Sets or groups of primers and probes are generated based on the target to be detected. The set of all possible primers and probes can include, for example, sequences that include the variability at every site based on the known viral genome, or the primers and probes can be generated based on a consensus sequence of the target. The primers and probes are generated such that the primers and probes are able to anneal to a particular sequence under high stringency conditions. For example, one of skill in the art recognizes that for any particular sequence, it is possible to provide more than one oligonucleotide sequence that will anneal to the particular target sequence, even under high stringency conditions. The set of primers and probes to be sampled includes, for example, all such oligonucleotides for all known and characterized influenza viruses. Alternatively, the primers and probes include all such oligonucleotides for a given consensus sequence for a target.

Typically, stringent hybridization and washing conditions are used for nucleic acid molecules over about 500 bp. Stringent hybridization conditions include a solution comprising about 1 M Na$^+$ at 25° C. to 30° C. below the Tm; e.g., 5×SSPE, 0.5% SDS, at 65° C.; see, Ausubel, et al., Current Protocols in Molecular Biology, Greene Publishing, 1995; Sambrook et al., Molecular Cloning: A Laboratory Manual, Cold Spring Harbor Press, 1989). Tm is dependent on both the G+C content and the concentration of salt ions, e.g., Na$^+$ and K$^+$ A formula to calculate the Tm of nucleic acid molecules greater than about 500 by is Tm=81.5+0.41(%(G+C))−log$_{10}$[Na$^+$]. Washing conditions are generally performed at least at equivalent stringency conditions as the hybridization. If the background levels are high, washing can be performed at higher stringency, such as around 15° C. below the Tm.

The set of primers and probes, once determined as described above, are optimized for hybridizing to a plurality of antibiotic resistance genes by employing scoring and/or ranking steps that provide a positive or negative preference or "weight" to certain nucleotides in a target nucleic acid strain sequence. If a consensus sequence is used to generate the full set of primers and probes, for example, then a particular primer sequence is scored for its ability to anneal to the corresponding sequence of every known native target sequence. Even if a probe were originally generated based on a consensus, the validation of the probe is in its ability to specifically anneal and detect every, or a large majority of, target sequences. The particular scoring or ranking steps performed depend upon the intended use for the primer and/or probe, the particular target nucleic acid sequence, and the number of resistance genes of that target nucleic acid sequence. The methods of the invention provide optimal primer and probe sequences because they hybridize to all or a subset of influenza viruses. Once optimized oligonucleotides are identified that can anneal to such genes, the sequences can then further be optimized for use, for example, in conjunction with another optimized sequence as a "primer set" or for use as a probe. A "primer set" is defined as at least one forward primer and one reverse primer.

Described herein are methods for using the primers and probes for producing a nucleic acid product, for example, comprising contacting one or more nucleic acid sequences of SEQ ID NOS: 1-53 to a sample comprising the influenza strain under conditions suitable for nucleic acid polymerization. The primers and probes can additionally be used to sequence the DNA of the influenza type(s), or used as diagnostics to, for example, detect the influenza type(s) in a clinical isolate sample, e.g., obtained from a subject, e.g., a mammalian subject. Particular combinations for amplifying DNA of influenza A, and/or influenza B, and/or 2009 influenza A/H1N1 and/or oseltamivir-resistant or sensitive 2009 influenza A/H1N1 include, for example, using at least one forward primer selected from the group consisting of: 1, 4, 7, 11, 13, 14, 19, 24, 27, 30, 33, 36, 39, 42, 45, 48, 51, 52, 53, 57 and 61; and at least one reverse primer selected from the group consisting of SEQ ID NOS: 3, 6, 9, 10, 12, 16, 18, 21, 23, 26, 28, 29, 32, 34, 35, 38, 41, 44, 47, 50, 55, 59 and 62.

Methods are described for detecting influenza A, and/or influenza B, and/or 2009 influenza A/H1N1 and/or oseltamivir-resistant or sensitive 2009 influenza A/H1N1 in a sample, for example, comprising (1) contacting at least one forward and reverse primer set, e.g., SEQ ID NOS: 1, 4, 7, 11, 13, 14, 19, 24, 27, 30, 33, 36, 39, 42, 45, 48, 51, 52, 53, 57 and 61 (forward primers); and 3, 6, 9, 10, 12, 16, 18, 21, 23, 26, 28, 29, 32, 34, 35, 38, 41, 44, 47, 50, 55, 59 and 62 (reverse primers) to a sample; (2) conducting an amplification; and (3) detecting the generation of an amplified product, wherein the generation of an amplified product indicates the presence of influenza A, and/or influenza B, and/or 2009 influenza A/H1N1 and/or oseltamivir-resistant or sensitive 2009 influenza A/H1N1 pathogens in a clinical isolate sample.

The detection of amplicons using probes described herein can be performed, for example, using a labeled probe, e.g., the probe comprising a nucleotide sequence selected from the group consisting of: SEQ ID NOS: 2, 5, 8, 15, 17, 20, 22, 25, 31, 37, 40, 43, 46, 49, 54, 56, 58, 60, and 63-67 that hybridizes to one of the strands of the amplicon generated by at least one forward and reverse primer set. The probe(s) can be, for example, fluorescently labeled, thereby indicating that the detection of the probe involves measuring the fluorescence of the sample of the bound probe, e.g., after bound probes have been isolated. Probes can also be fluorescently labeled in such a way, for example, such that they only fluoresce upon hybridizing to their target, thereby eliminating the need to isolate hybridized probes. The probe can also comprise a fluorescent reporter moiety and a quencher of fluorescence moiety. Upon probe hybridization with the amplified product, the exonuclease activity of a DNA polymerase can be used to dissociate the probe's reporter and quencher, resulting in the unquenched emission of fluorescence, which is detected. An increase in the amplified product causes a proportional increase in fluorescence, due to cleavage of the probe and release of the reporter moiety of the probe. The amplified product is quantified in real time as it accumulates. For multiplex reactions involving more than one distinct probe, each of the probes can be labeled with a different distinguishable and detectable label.

The probes can be molecular beacons. Molecular beacons are single-stranded probes that form a stem-loop structure. A fluorophore can be, for example, covalently linked to one end of the stem and a quencher can be covalently linked to the other end of the stem forming a stem hybrid. When a molecular beacon hybridizes to a target nucleic acid sequence, the probe undergoes a conformational change that results in the dissociation of the stem hybrid and, thus the fluorophore and the quencher move away from each other, enabling the probe to fluoresce brightly. Molecular beacons can be labeled with differently colored fluorophores to detect different target sequences. Any of the probes described herein can be modified and utilized as molecular beacons.

The probes can be conjugated to a minor groove binder (MGB) group. This increases the stability of the probe template hybrid and reduces the tolerance for mismatches, which results in better discriminatory properties. With MGBs, the added functionality is due to a peptide moiety conjugated to the nucleic acid sequence that alters the binding properties of the probe.

The probes can alternatively be modified using locked nucleic acid (LNA) technology (see Kaur, H. et al., *Biochemistry*, 45:7347-55, 2006; and You, Y. et al., *Nucl. Acids Res.*, 34:e60, 2006). LNA is a modified nucleic acid that is incorporated into the probe, replacing one or more of the nucleotides, thus altering the way that region of the probe binds to its complementary target sequence. For example, some of the nucleic probes of the present invention that detect oseltamivir resistance or sensitivity are modified using LNAs. A LNA, often referred to as inaccessible RNA, is a modified RNA nucleotide. The ribose moiety of an LNA nucleotide is modified with an extra bridge connecting the 2' and 4' carbons. The bridge "locks" the ribose in the 3'-endo structural conformation, which is often found in the A-form of DNA or RNA. LNA nucleotides can be mixed with DNA or RNA bases in the oligonucleotide whenever desired. The locked ribose conformation enhances base stacking and backbone pre-organization. This significantly increases the thermal stability (melting temperature) of oligonucleotides.

Primer or probe sequences can be ranked according to specific hybridization parameters or metrics that assign a score value indicating their ability to anneal to viral strains under highly stringent conditions. Where a primer set is being scored, a "first" or "forward" primer is scored and the "second" or "reverse"-oriented primer sequences can be optimized similarly but with potentially additional parameters, followed by an optional evaluation for primer dimmers, for example, between the forward and reverse primers.

The scoring or ranking steps that are used in the methods of determining the primers and probes include, for example, the following parameters: a target sequence score for the target nucleic acid sequence(s), e.g., the PriMD® score; a mean conservation score for the target nucleic acid sequence(s); a mean coverage score for the target nucleic acid sequence(s); 100% conservation score of a portion (e.g., 5' end, center, 3' end) of the target nucleic acid sequence(s); a species score; a strain score; a subtype score; a serotype score; an associated disease score; a year score; a country of origin score; a duplicate score; a patent score; and a minimum qualifying score. Other parameters that are used include, for example, the number of mismatches, the number of critical mismatches (e.g., mismatches that result in the predicted failure of the sequence to anneal to a target sequence), the number of native strain sequences that contain critical mismatches, and predicted Tm values. The term "Tm" refers to the temperature at which a population of double-stranded nucleic acid molecules becomes half-dissociated into single strands. Methods for calculating the Tm of nucleic acids are known in the art (Berger and Kimmel (1987) *Meth. Enzymol.*, Vol. 152: Guide To Molecular Cloning Techniques, San Diego: Academic Press, Inc. and Sambrook et al. (1989) Molecular Cloning: A Laboratory Manual, (2nd ed.) Vols. 1-3, Cold Spring Harbor Laboratory).

The resultant scores represent steps in determining nucleotide or whole target nucleic acid sequence preference, while tailoring the primer and/or probe sequences so that they hybridize to a plurality of target nucleic acid sequences. The methods of determining the primers and probes also can comprise the step of allowing for one or more nucleotide changes when determining identity between the candidate primer and probe sequences and the target nucleic acid sequences, or their complements.

In another embodiment, the methods of determining the primers and probes comprise the steps of comparing the candidate primer and probe nucleic acid sequences to "exclusion nucleic acid sequences" and then rejecting those candidate nucleic acid sequences that share identity with the exclusion nucleic acid sequences. In another embodiment, the methods comprise the steps of comparing the candidate primer and probe nucleic acid sequences to "inclusion nucleic acid sequences" and then rejecting those candidate nucleic acid sequences that do not share identity with the inclusion nucleic acid sequences.

In other embodiments of the methods of determining the primers and probes, optimizing primers and probes comprises using a polymerase chain reaction (PCR) penalty score formula comprising at least one of a weighted sum of: primer Tm—optimal Tm; difference between primer Tms; amplicon length—minimum amplicon length; and distance between the primer and a TaqMan® probe. The optimizing step also can comprise determining the ability of the candidate sequence to hybridize with the most target nucleic acid strain sequences (e.g., the most target organisms or genes). In another embodiment, the selecting or optimizing step comprises determining which sequences have mean conservation scores closest to 1, wherein a standard of deviation on the mean conservation scores is also compared.

In other embodiments, the methods further comprise the step of evaluating which target nucleic acid sequences are hybridized by an optimal forward primer and an optimal reverse primer, for example, by determining the number of base pair differences between target nucleic acid sequences in a database. For example, the evaluating step can comprise performing an in silico polymerase chain reaction, involving (1) rejecting the forward primer and/or reverse primer if it does not meet inclusion or exclusion criteria; (2) rejecting the forward primer and/or reverse primer if it does not amplify a medically valuable nucleic acid; (3) conducting a BLAST analysis to identify forward primer sequences and/or reverse primer sequences that overlap with a published and/or patented sequence; (4) and/or determining the secondary structure of the forward primer, reverse primer, and/or target. In an embodiment, the evaluating step includes evaluating whether the forward primer sequence, reverse primer sequence, and/or probe sequence hybridizes to sequences in the database other than the nucleic acid sequences that are representative of the target strains.

The present invention provides oligonucleotides that have preferred primer and probe qualities. These qualities are specific to the sequences of the optimized probes, however, one of skill in the art would recognize that other molecules with similar sequences could also be used. The oligonucleotides provided herein comprise a sequence that shares at least about 60-70% identity with a sequence described in Table 4. In addition, the sequences can be incorporated into longer sequences, provided they function to specifically anneal to and identify viral strains. In another embodiment, the invention provides a nucleic acid comprising a sequence that shares at least about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identity with the sequences of Table 4 or complement thereof. The terms "homology" or "identity" or "similarity" refer to sequence relationships between two nucleic acid molecules and can be determined by comparing a nucleotide position in each sequence when aligned for purposes of comparison. The term "homology" refers to the relatedness of two nucleic acid or protein sequences. The term "identity" refers to the degree to which nucleic acids are the same between two sequences. The term "similarity" refers to the degree to which nucleic acids are the same, but includes neutral degenerate nucleotides that can be substituted within a codon without changing the amino acid identity of the codon, as is well known in the art. The primer and/or probe nucleic acid sequences of the invention are complementary to the target nucleic acid sequence. The probe and/or primer nucleic acid sequences of the invention are optimal for identifying numerous strains of a target nucleic acid, e.g., influenza viruses. In an embodiment, the nucleic acids of the invention are primers for the synthesis (e.g., amplification) of target nucleic acid sequences and/or probes for identification, isolation, detection, or analysis of target nucleic acid sequences, e.g., an amplified target nucleic acid that is amplified using the primers of the invention.

The present oligonucleotides hybridize with more than one influenza type (as determined by differences in its sequence). The probes and primers provided herein can, for example, allow for the detection of currently identified influenza types or a subset thereof. In addition, the primers and probes of the present invention, depending on the influenza sequence(s), can allow for the detection of previously unidentified influenza sequences. The methods of the invention provide for optimal primers and probes, and sets thereof, and combinations of sets thereof, which can hybridize with a larger number of targets than available primers and probes.

In other aspects, the invention also provides vectors (e.g., plasmid, phage, expression), cell lines (e.g., mammalian, insect, yeast, bacterial, viral), and kits comprising any of the sequences of the invention described herein. The invention further provides known or previously unknown target nucleic acid strain sequences that are identified, for example, using the methods of the invention. In an embodiment, the target nucleic acid sequence is an amplification product. In another embodiment, the target nucleic acid sequence is a native or synthetic nucleic acid. The primers, probes, and target nucleic acid sequences, vectors, cell lines, and kits can have any number of uses, such as diagnostic, investigative, confirmatory, monitoring, predictive or prognostic.

Diagnostic kits that comprise one or more of the oligonucleotides described herein, which are useful for screening for and/or detecting the presence of influenza in an individual and/or from a sample, are provided herein. An individual can be a human male, human female, human adult, human child, or human fetus. A sample includes any item, surface, material, clothing, or environment, in which it may be desirable to test for the presence of influenza virus(es). Thus, for instance, the present invention includes testing door handles, faucets, table surfaces, elevator buttons, chairs, toilet seats, sinks, kitchen surfaces, children's cribs, bed linen, pillows, keyboards, and so on, for the presence of influenza virus(es).

A probe of the present invention can comprise a label such as, for example, a fluorescent label, a chemiluminescent label, a radioactive label, biotin, gold, dendrimers, aptamer, enzymes, proteins, quenchers and molecular motors. In an embodiment, the probe is a hydrolysis probe, such as, for example, a TaqMan® probe. In other embodiments, the probes of the invention are molecular beacons, any fluorescent probes, probes modified with locked nucleic acids and probes that are replaced by any double stranded DNA binding dyes (e.g., SYBR Green® 1).

Oligonucleotides of the present invention do not only include primers that are useful for conducting the aforementioned amplification reactions, but also include oligonucleotides that are attached to a solid support, such as, for example, a microarray, multiwell plate, column, bead, glass slide, polymeric membrane, glass microfiber, plastic tubes, cellulose, and carbon nanostructures. Hence, detection of influenza viruses can be performed by exposing such an oligonucleotide-covered surface to a sample such that the binding of a complementary strain DNA sequence to a surface-attached oligonucleotide elicits a detectable signal or reaction.

Oligonucleotides of the present invention also include primers for isolating and sequencing nucleic acid sequences derived from any identified or yet to be isolated and identified influenza virus.

One embodiment of the invention uses solid support-based oligonucleotide hybridization methods to detect gene expression. Solid support-based methods suitable for practicing the present invention are widely known and are described (PCT application WO 95/11755; Huber et al., *Anal. Biochem.*, 299: 24, 2001; Meiyanto et al., *Biotechniques*, 31:406, 2001; Relogio et al., *Nucleic Acids Res.*, 30:e51, 2002; the contents of which are incorporated herein by reference in their entirety). Any solid surface to which oligonucleotides can be bound, covalently or non-covalently, can be used. Such solid supports include, but are not limited to, filters, polyvinyl chloride dishes, silicon or glass based chips.

In certain embodiments, the nucleic acid molecule can be directly bound to the solid support or bound through a linker arm, which is typically positioned between the nucleic acid sequence and the solid support. A linker arm that increases the distance between the nucleic acid molecule and the substrate can increase hybridization efficiency. There are a number of ways to position a linker arm. In one common approach, the solid support is coated with a polymeric layer that provides linker arms with a plurality of reactive ends/sites. A common example of this type is glass slides coated with polylysine (U.S. Pat. No. 5,667,976, the contents of which are incorporated herein by reference in its entirety), which are commercially available. Alternatively, the linker arm can be synthesized as part of or conjugated to the nucleic acid molecule, and then this complex is bonded to the solid support. One approach, for example, takes advantage of the extremely high affinity biotin-streptavidin interaction. The streptavidin-biotinylated reaction is stable enough to withstand stringent washing conditions and is sufficiently stable that it is not cleaved by laser pulses used in some detection systems, such as matrix-assisted laser desorption/ionization time of flight (MALDI-TOF) mass spectrometry. Therefore, streptavidin can be covalently attached to a solid support, and a biotinylated nucleic acid molecule will bind to the streptavidin-coated surface. In one version of this method, an amino-coated silicon wafer is reacted with the n-hydroxysuccinimido-ester of biotin and complexed with streptavidin. Biotinylated oligonucleotides are bound to the surface at a concentration of about 20 fmol DNA per mm$^2$.

One can alternatively directly bind DNA to the support using carbodiimides, for example. In one such method, the support is coated with hydrazide groups, and then treated with carbodiimide. Carboxy-modified nucleic acid molecules are then coupled to the treated support. Epoxide-based chemistries are also being employed with amine modified oligonucleotides. Other chemistries for coupling nucleic acid molecules to solid substrates are known to those of skill in the art.

The nucleic acid molecules, e.g., the primers and probes of the present invention, must be delivered to the substrate material, which is suspected of containing or is being tested for the presence of influenza virus(es). Because of the miniaturization of the arrays, delivery techniques must be capable of positioning very small amounts of liquids in very small regions, very close to one another and amenable to automation. Several techniques and devices are available to achieve such delivery. Among these are mechanical mechanisms (e.g., arrayers from GeneticMicroSystems, MA, USA) and ink jet technology. Very fine pipets can also be used.

Other formats are also suitable within the context of this invention. For example, a 96-well format with fixation of the nucleic acids to a nitrocellulose or nylon membrane can also be employed.

After the nucleic acid molecules have been bound to the solid support, it is often useful to block reactive sites on the solid support that are not consumed in binding to the nucleic acid molecule. In the absence of the blocking step, excess primers and/or probes can, to some extent, bind directly to the solid support itself, giving rise to non-specific binding. Non-specific binding can sometimes hinder the ability to detect low levels of specific binding. A variety of effective blocking agents (e.g., milk powder, serum albumin or other proteins with free amine groups, polyvinylpyrrolidine) can be used and others are known to those skilled in the art (U.S. Pat. No. 5,994,065, the contents of which are incorporated herein by reference in their entirety). The choice depends at least in part upon the binding chemistry.

One embodiment uses oligonucleotide arrays, e.g., microarrays, that can be used to simultaneously observe the expression of a number of influenza virus(es). Oligonucleotide arrays comprise two or more oligonucleotide probes provided on a solid support, wherein each probe occupies a unique location on the support. The location of each probe can be predetermined, such that detection of a detectable signal at a given location is indicative of hybridization to an oligonucleotide probe of a known identity. Each predetermined location can contain more than one molecule of a probe, but each molecule within the predetermined location has an identical sequence. Such predetermined locations are termed features. There can be, for example, from 2, 10, 100, 1,000, 2,000 or 5,000 or more of such features on a single solid support. In one embodiment, each oligonucleotide is located at a unique position on an array at least 2, at least 3, at least 4, at least 5, at least 6, or at least 10 times.

Oligonucleotide probe arrays for detecting gene expression can be made and used according to conventional techniques described (Lockhart et al., *Nat. Biotech.*, 14:1675-1680, 1996; McGall et al., *Proc. Natl. Acad. Sci. USA*, 93:13555, 1996; Hughes et al., *Nat. Biotechnol.*, 19:342, 2001). A variety of oligonucleotide array designs are suitable for the practice of this invention.

Generally, a detectable molecule, also referred to herein as a label, can be incorporated or added to an array's probe nucleic acid sequences. Many types of molecules can be used within the context of this invention. Such molecules include, but are not limited to, fluorochromes, chemiluminescent molecules, chromogenic molecules, radioactive molecules, mass spectrometry tags, proteins, and the like. Other labels will be readily apparent to one skilled in the art.

Oligonucleotide probes used in the methods of the present invention, including microarray techniques, can be generated using PCR. PCR primers used in generating the probes are chosen, for example, based on the sequences of Table 4. In one embodiment, oligonucleotide control probes also are used. Exemplary control probes can fall into at least one of three categories referred to herein as (1) normalization controls, (2) expression level controls and (3) negative controls. In microarray methods, one or more of these control probes can be provided on the array with the inventive cell cycle gene-related oligonucleotides.

Normalization controls correct for dye biases, tissue biases, dust, slide irregularities, malformed slide spots, etc. Normalization controls are oligonucleotide or other nucleic acid probes that are complementary to labeled reference oligonucleotides or other nucleic acid sequences that are added to the nucleic acid sample to be screened. The signals obtained from the normalization controls, after hybridization, provide a control for variations in hybridization conditions, label intensity, reading efficiency and other factors that can cause the signal of a perfect hybridization to vary between arrays. The normalization controls also allow for the semi-quantification of the signals from other features on the microarray. In one embodiment, signals (e.g., fluorescence intensity or radioactivity) read from all other probes used in the method are divided by the signal from the control probes, thereby normalizing the measurements.

Virtually any probe can serve as a normalization control. Hybridization efficiency varies, however, with base composition and probe length. Preferred normalization probes are selected to reflect the average length of the other probes being used, but they also can be selected to cover a range of lengths. Further, the normalization control(s) can be selected to reflect the average base composition of the other probe(s) being used. In one embodiment, only one or a few normalization probes are used, and they are selected such that they hybridize well (i.e., without forming secondary structures) and do not match any test probes. In one embodiment, the normalization controls are mammalian genes.

"Negative control" probes are not complementary to any of the test oligonucleotides (i.e., the inventive cell cycle gene-related oligonucleotides), normalization controls, or expression controls. In one embodiment, the negative control is a mammalian gene that is not complementary to any other sequence in the sample.

The terms "background" and "background signal intensity" refer to hybridization signals resulting from non-specific binding or other interactions between the labeled target nucleic acids (e.g., mRNA present in the biological sample) and components of the oligonucleotide array. Background signals also can be produced by intrinsic fluorescence of the array components themselves. A single background signal can be calculated for the entire array, or a different background signal can be calculated for each target nucleic acid. In one embodiment, background is calculated as the average hybridization signal intensity for the lowest 5 to 10 percent of the oligonucleotide probes being used, or, where a different background signal is calculated for each target gene, for the lowest 5 to 10 percent of the probes for each gene. Where the oligonucleotide probes corresponding to a particular target hybridize well and, hence, appear to bind specifically to a target sequence, they should not be used in a background signal calculation. Alternatively, background can be calculated as the average hybridization signal intensity produced by hybridization to probes that are not complementary to any sequence found in the sample (e.g., probes directed to nucleic acids of the opposite sense or to genes not found in the sample). In microarray methods, background can be calculated as the average signal intensity produced by regions of the array that lack any oligonucleotides probes at all.

In an alternative embodiment, the nucleic acid molecules are directly or indirectly coupled to an enzyme. Following hybridization, a chromogenic substrate is applied and the colored product is detected by a camera, such as a charge-coupled camera. Examples of such enzymes include alkaline phosphatase, horseradish peroxidase and the like. A probe can be labeled with an enzyme or, alternatively, the probe is labeled with a moiety that is capable of binding to another moiety that is linked to the enzyme. For example, in the biotin-streptavidin interaction, the streptavidin is conjugated to an enzyme such as horseradish peroxidase (HRP). A chromogenic substrate is added to the reaction and is processed/cleaved by the enzyme. The product of the cleavage forms a color, either in the UV or visible spectrum. In another embodiment, streptavidin alkaline phosphatase can be used in a labeled streptavidin-biotin immunoenzymatic antigen detection system.

The invention also provides methods of labeling nucleic acid molecules with cleavable mass spectrometry tags (CMST; U.S. Patent Application No. 60/279,890). After an assay is complete, and the uniquely CMST-labeled probes are distributed across the array, a laser beam is sequentially directed to each member of the array. The light from the laser beam both cleaves the unique tag from the tag-nucleic acid molecule conjugate and volatilizes it. The volatilized tag is directed into a mass spectrometer. Based on the mass spectrum of the tag and knowledge of how the tagged nucleotides were prepared, one can unambiguously identify the nucleic acid molecules to which the tag was attached (WO 9905319).

The nucleic acids, primers and probes of the present invention can be labeled readily by any of a variety of techniques. When the diversity panel is generated by amplification, the nucleic acids can be labeled during the reaction by incorporation of a labeled dNTP or use of labeled amplification primer. If the amplification primers include a promoter for an RNA polymerase, a post-reaction labeling can be achieved by synthesizing RNA in the presence of labeled NTPs. Amplified fragments that were unlabeled during amplification or unamplified nucleic acid molecules can be labeled by one of a number of end labeling techniques or by a transcription method, such as nick-translation, random-primed DNA synthesis. Details of these methods are known to one of skill in the art and are set out in methodology books. Other types of labeling reactions are performed by denaturation of the nucleic acid molecules in the presence of a DNA-binding molecule, such as RecA, and subsequent hybridization under conditions that favor the formation of a stable RecA-incorporated DNA complex.

In another embodiment, PCR-based methods are used to detect gene expression. These methods include reverse-transcriptase-mediated polymerase chain reaction (RT-PCR) including real-time and endpoint quantitative reverse-transcriptase-mediated polymerase chain reaction (Q-RTPCR). These methods are well known in the art. For example, methods of quantitative PCR can be carried out using kits and methods that are commercially available from, for example, Applied BioSystems and Stratagene®. See also Kochanowski, Quantitative PCR Protocols (Humana Press, 1999); Innis et al., supra.; Vandesompele et al., Genome Biol., 3: RESEARCH0034, 2002; Stein, Cell Mol. Life Sci. 59:1235, 2002.

The forward and reverse amplification primers and internal hybridization probe is designed to hybridize specifically and uniquely with one nucleotide sequence derived from the transcript of a target gene. In one embodiment, the selection criteria for primer and probe sequences incorporates constraints regarding nucleotide content and size to accommodate TaqMan® requirements. SYBR Green® can be used as a probe-less Q-RTPCR alternative to the TaqMac®-type assay, discussed above (ABI Prism® 7900 Sequence Detection System User Guide Applied Biosystems, chap. 1-8, App. A-F. (2002)). A device measures changes in fluorescence emission intensity during PCR amplification. The measurement is done in "real time," that is, as the amplification product accumulates in the reaction. Other methods can be used to measure changes in fluorescence resulting from probe digestion. For example, fluorescence polarization can distinguish between large and small molecules based on molecular tumbling (U.S. Pat. No. 5,593,867).

The primers and probes of the present invention may anneal to or hybridize to various influenza genetic material or genetic material derived therefrom, or other genetic material derived therefrom, such as RNA, DNA, cDNA, or a PCR product.

A "sample" that is tested for the presence of influenza virus(es) includes, but is not limited to a tissue sample, such as, for example, saliva, fluids collected from the ear, eye, mouth, and respiratory airways, sputum, skin, tears, oropharyngeal swabs, nasopharyngeal swabs, throat swabs, skin swabs, nasal aspirates, and nasal wash. The tissue sample may be fresh, fixed, preserved, or frozen. A sample also includes any item, surface, material, or clothing, or environment, in which it may be desirable to test for the presence of influenza virus(es). Thus, for instance, the present invention includes testing door handles, faucets, table surfaces, elevator buttons, chairs, toilet seats, sinks, kitchen surfaces, children's cribs, bed linen, pillows, keyboards, and so on, for the presence of influenza virus(es).

The target nucleic acid strain that is amplified may be RNA or DNA or a modification thereof. Thus, the amplifying step can comprise isothermal or non-isothermal reactions, such as polymerase chain reaction, Scorpion® primers, molecular beacons, SimpleProbes®, HyBeacons®, cycling probe technology, Invader Assay, self-sustained sequence replication, nucleic acid sequence-based amplification, ramification amplifying method, hybridization signal amplification method, rolling circle amplification, multiple displacement amplification, thermophilic strand displacement amplification, transcription-mediated amplification, ligase chain reaction, signal mediated amplification of RNA, split promoter amplification, Q-Beta replicase, isothermal chain reaction, one cut event amplification, loop-mediated isothermal amplification, molecular inversion probes, ampliprobe, headloop DNA amplification, and ligation activated transcription. The amplifying step can be conducted on a solid support, such as a multiwell plate, array, column, bead, glass slide, polymeric membrane, glass microfiber, plastic tubes, cellulose, and carbon nanostructures. The amplifying step also comprises in situ hybridization. The detecting step can comprise gel electrophoresis, fluorescence resonant energy transfer, or hybridization to a labeled probe, such as a probe labeled with biotin, at least one fluorescent moiety, an antigen, a molecular weight tag, and a modifier of probe Tm. The detection step can also comprise the incorporation of a label (e.g., fluorescent or radioactive) during an extension reaction. The detecting step comprises measuring fluorescence, mass, charge, and/or chemiluminescence.

The target nucleic acid strain may not need amplification and may be RNA or DNA or a modification thereof. If amplification is not necessary, the target nucleic acid strain can be denatured to enable hybridization of a probe to the target nucleic acid sequence.

Hybridization may be detected in a variety of ways and with a variety of equipment. In general, the methods can be categorized as those that rely upon detectable molecules incorporated into the diversity panels and those that rely upon measurable properties of double-stranded nucleic acids (e.g., hybridized nucleic acids) that distinguish them from single-stranded nucleic acids (e.g., unhybridized nucleic acids). The latter category of methods includes intercalation of dyes, such as, for example, ethidium bromide, into double-stranded nucleic acids, differential absorbance properties of double and single stranded nucleic acids, binding of proteins that preferentially bind double-stranded nucleic acids, and the like.

EXEMPLIFICATION

Example 1

Scoring a Set of Predicted Annealing Oligonucleotides

Each of the sets of primers and probes selected is ranked by a combination of methods as individual primers and probes and as a primer/probe set. This involves one or more methods of ranking (e.g., joint ranking, hierarchical ranking , and serial ranking) where sets of primers and probes are eliminated or included based on any combination of the following criteria, and a weighted ranking again based on any combination of the following criteria, for example: (A) Percentage Identity to Target Strains; (B) Conservation Score; (C) Coverage Score; (D) Strain/Subtype/Serotype Score; (E) Associated Disease Score; (F) Duplicates Sequences Score; (G) Year and Country of Origin Score; (H) Patent Score, and (I) Epidemiology Score.

(A) Percentage Identity

A percentage identity score is based upon the number of target nucleic acid strain (e.g., native) sequences that can hybridize with perfect conservation (the sequences are perfectly complimentary) to each primer or probe of a primer set and probe set. If the score is less than 100%, the program ranks additional primer set and probe sets that are not perfectly conserved. This is a hierarchical scale for percent identity starting with perfect complimentarity, then one base degeneracy through to the number of degenerate bases that would provide the score closest to 100%. The position of these degenerate bases would then be ranked. The methods for calculating the conservation is described under section B.

(i) Individual Base Conservation Score

A set of conservation scores is generated for each nucleotide base in the consensus sequence and these scores represent how many of the target nucleic acid strains sequences have a particular base at this position. For example, a score of 0.95 for a nucleotide with an adenosine, and 0.05 for a nucleotide with a cytidine means that 95% of the native sequences have an A at that position and 5% have a C at that position. A perfectly conserved base position is one where all the target nucleic acid strain sequences have the same base (either an A, C, G, or T/U) at that position. If there is an equal number of bases (e.g., 50% A & 50% T) at a position, it is identified with an N.

(ii) Candidate Primer/Probe Sequence Conservation

An overall conservation score is generated for each candidate primer or probe sequence that represents how many of the target nucleic acid strain sequences will hybridize to the primers or probes. A candidate sequence that is perfectly complimentary to all the target nucleic acid strain sequences will have a score of 1.0 and rank the highest. For example, illustrated below in Table 3 are three different 10-base candidate probe sequences that are targeted to different regions of a consensus target nucleic acid strain sequence. Each candidate probe sequence is compared to a total of 10 native sequences.

TABLE 3

```
                                            (SEQ ID NO: 367)
#1.  A    A    A    C    A    C    G    T    G    C
     0.7  1.0  1.0  1.0  1.0  1.0  1.0  1.0  1.0  1.0
```
→Number of target nucleic acid strain sequences that are perfectly complimentary-7. Three out of the ten sequences do not have an A at position 1.

```
                                            (SEQ ID NO: 368)
#2.  C    C    T    T    G    T    T    C    C    A
     1.0  0.9  1.0  0.9  0.9  1.0  1.0  1.0  1.0  1.0
```
→Number of target nucleic acid strain sequences that are perfectly complimentary-7, 8, or 9. At least one target nucleic acid strain does not have a C at position 2, T at position 4, or G at position 5. These differences may all be on one target nucleic acid strain molecule or may be on two or three separate molecules.

```
                                            (SEQ ID NO: 369)
#3.  C    A    G    G    G    A    C    G    A    T
     1.0  1.0  1.0  1.0  1.0  0.9  0.8  1.0  1.0  1.0
```
→Number of target nucleic acid strain sequences that are perfectly complimentary-7 or 8. At least one target nucleic acid strain does not have an A at position 6 and at least two target nucleic acid strain do not have a C at position 7. These differences may all be on one target nucleic acid strain molecule or may be on t- wo separate molecules.

A simple arithmetic mean for each candidate sequence would generate the same value of 0.97. The number of target nucleic acid strain sequences identified by each candidate probe sequence, however, can be very different. Sequence #1 can only identify 7 native sequences because of the 0.7 (out of 1.0) score by the first base—A. Sequence #2 has three bases each with a score of 0.9; each of these could represent a different or shared target nucleic acid strain sequence. Consequently, Sequence #2 can identify 7, 8 or 9 target nucleic acid strain sequences. Similarly, Sequence #3 can identify 7 or 8 of the target nucleic acid strain sequences. Sequence #2 would, therefore, be the best choice if all the three bases with a score of 0.9 represented the same 9 target nucleic acid strain sequences.

(iii) Overall Conservation Score of the Primer and Probe Set—Percent Identity

The same method described in (ii) when applied to the complete primer set and probe set will generate the percent identity for the set (see A above). For example, using the same sequences illustrated above, if Sequences #1 and #2 are primers and Sequence #3 is a probe, then the percent identity for the target can be calculated from how many of the target nucleic acid sequences are identified with perfect complementarity to all three primer/probe sequences. The percent identity could be no better than 0.7 (7 out of 10 target nucleic acid strain sequences) but as little as 0.1 if each of the degenerate bases reflects a different target nucleic acid strain sequence. Again, an arithmetic mean of these three sequences would be 0.97. As none of the above examples were able to capture all the target nucleic acid strain sequences because of the degeneracy (scores of less than 1.0), the ranking system takes into account that a certain amount of degeneracy can be tolerated under normal hybridization conditions, for example, during a polymerase chain reaction. The ranking of these degeneracies is described in (iv) below.

An in silico evaluation determines how many native sequences (e.g., original sequences submitted to public databases) are identified by a given candidate primer/probe set. The ideal candidate primer/probe set is one that can perform PCR and the sequences are perfectly complementary to all the known native sequences that were used to generate the consensus sequence. If there is no such candidate, then the sets are ranked according to how many degenerate bases can be accepted and still hybridize to just the target sequence during the PCR and yet identify all the native sequences.

The hybridization conditions, for TaqMan® as an example, are: 10-50 mM Tris-HCl pH 8.3, 50 mM KCl, 0.1-0.2% Triton® X-100 or 0.1% Tween®, 1-5 mM $MgCl_2$. The hybridization is performed at 58-60° C. for the primers and 68-70° C. for the probe. The in silico PCR identifies native sequences that are not amplifiable using the candidate primers and probe set. The rules can be as simple as counting the number of degenerate bases to more sophisticated approaches based on exploiting the PCR criteria used by the PriMD® software. Each target nucleic acid strain sequence has a value or weight (see Score assignment above). If the failed target nucleic acid strain sequence is medically valuable, the primer/probe set is rejected. This in silico analysis provides a degree of confidence for a given genotype and is important when new sequences are added to the databases. New target nucleic acid strain sequences are automatically entered into both the "include" and "exclude" categories. Published primer and probes will also be ranked by the PriMD software.

(iv) Position (5' to 3') Of The Base Conservation Score

In an embodiment, primers do not have bases in the terminal five positions at the 3' end with a score less than 1. This is one of the last parameters to be relaxed if the method fails to select any candidate sequences. The next best candidate having a perfectly conserved primer would be one where the poorer conserved positions are limited to the terminal bases at the 5' end. The closer the poorer conserved position is to the 5' end, the better the score. For probes, the position criteria are different. For example, with a TaqMan® probe, the most destabilizing effect occurs in the center of the probe. The 5' end of the probe is also important as this contains the reporter molecule that must be cleaved, following hybridization to the target, by the polymerase to generate a sequence-specific signal. The 3' end is less critical. Therefore, a sequence with a perfectly conserved middle region will have the higher score. The remaining ends of the probe are ranked in a similar fashion to the 5' end of the primer. Thus, the next best candidate to a perfectly conserved TaqMan® probe would be one where the poorer conserved positions are limited to the terminal bases at either the 5' or 3' ends. The hierarchical scoring will select primers with only one degeneracy first, then primers with two degeneracies next and so on. The relative position of each degeneracy will then be ranked favoring those that are closest to the 5' end of the primers and those closest to the 3' end of the TaqMan® probe. If there are two or more degenerate bases in a primer and probe set the ranking will initially select the sets where the degeneracies occur on different sequences.

B. Coverage Score

The total number of aligned sequences is considered under a coverage score. A value is assigned to each position based on how many times that position has been reported or sequenced. Alternatively, coverage can be defined as how representative the sequences are of the known strains, subtypes etc., or their relevance to a certain diseases. For example, the target nucleic acid strain sequences for a particular gene may be very well conserved and show complete coverage but certain strains are not represented in those sequences.

A sequence is included if it aligns with any part of the consensus sequence, which is usually a whole gene or a functional unit, or has been described as being a representative of this gene. Even though a base position is perfectly conserved it may only represent a fraction of the total number of sequences (for example, if there are very few sequences). For example, region A of a gene shows a 100% conservation from 20 sequence entries while region B in the same gene shows a 98% conservation but from 200 sequence entries. There is a relationship between conservation and coverage if the sequence shows some persistent variability. As more sequences are aligned, the conservation score falls, but this effect is lessened as the number of sequences gets larger. Unless the number of sequences is very small (e.g., under 10) the value of the coverage score is small compared to that of the conservation score. To obtain the best consensus sequence, artificial spaces are allowed to be introduced. Such spaces are not considered in the coverage score.

C. Strain/Subtype/Serotype Score

A value is assigned to each strain or subtype or serotype based upon its relevance to a disease. For example, viral strains and/or species that are linked to high frequencies of infection will have a higher score than strains that are generally regarded as benign. The score is based upon sufficient evidence to automatically associate a particular strain with a disease. For example, certain strains of adenovirus are not associated with diseases of the upper respiratory system. Accordingly, there will be sequences included in the consensus sequence that are not associated with diseases of the upper respiratory system.

D. Associated Disease Score

The associated disease score pertains to strains that are not known to be associated with a particular disease (to differentiate from D above). Here, a value is assigned only if the submitted sequence is directly linked to the disease and that disease is pertinent to the assay.

E. Duplicate Sequences Score

If a particular sequence has been sequenced more than once it will have an effect on representation, for example, a strain that is represented by 12 entries in GenBank of which six are identical and the other six are unique. Unless the identical sequences can be assigned to different strains/subtypes (usually by sequencing other gene or by immunology methods) they will be excluded from the scoring.

F. Year and Country of Origin Score

The year and country of origin scores are important in terms of the age of the human population and the need to provide a product for a global market. For example, strains identified or collected many years ago may not be relevant today. Furthermore, it is probably difficult to obtain samples that contain these older strains. Certain divergent strains from more obscure countries or sources may also be less relevant to the locations that will likely perform clinical tests, or may be more important for certain countries (e.g., North America, Europe, or Asia).

G. Patent Score

Candidate target strain sequences published in patents are searched electronically and annotated such that patented regions are excluded. Alternatively, candidate sequences are checked against a patented sequence database.

H. Minimum Qualifying Score

The minimum qualifying score is determined by expanding the number of allowed mismatches in each set of candidate primers and probes until all possible native sequences are represented (e.g., has a qualifying hit).

I. Other

A score is given to based on other parameters, such as relevance to certain patients (e.g., pediatrics, immunocompromised) or certain therapies (e.g., target those strains that respond to treatment) or epidemiology. The prevalence of an organism/strain and the number of times it has been tested for in the community can add value to the selection of the candidate sequences. If a particular strain is more commonly tested then selection of it would be more likely. Strain identification can be used to select better vaccines.

Example 2

Primer/Probe Evaluation

Once the candidate primers and probes have received their scores and have been ranked, they are evaluated using any of a number of methods of the invention, such as BLAST analysis and secondary structure analysis.

A. BLAST Analysis

The candidate primer/probe sets are submitted to BLAST analysis to check for possible overlap with any published sequences that might be missed by the Include/Exclude function. It also provides a useful summary.

B. Secondary Structure

The methods of the present invention include analysis of nucleic acid secondary structure. This includes the structures of the primers and/or probes, as well as their intended target strain sequences. The methods and software of the invention predict the optimal temperatures for annealing, but assumes that the target (e.g., RNA or DNA) does not have any significant secondary structure. For example, if the starting material is RNA, the first stage is the creation of a complimentary strand of DNA (cDNA) using a specific primer. This is usually performed at temperatures where the RNA template can have significant secondary structure thereby preventing the annealing of the primer. Similarly, after denaturation of a double stranded DNA target (for example, an amplicon after PCR), the binding of the probe is dependent on there being no major secondary structure in the amplicon.

The methods of the invention can either use this information as a criteria for selecting primers and probes or evaluate any secondary structure of a selected sequence, for example, by cutting and pasting candidate primer or probe sequences into a commercial internet link that uses software dedicated to analyzing secondary structure, such as, for example, MFOLD (Zuker et al. (1999) Algorithms and Thermodynamics for RNA Secondary Structure Prediction: A Practical Guide in RNA Biochemistry and Biotechnology, J. Barciszewski and B. F. C. Clark, eds., NATO ASI Series, Kluwer Academic Publishers).

C. Evaluating the Primer and Probe Sequences

The methods and software of the invention may also analyze any nucleic acid sequence to determine its suitability in a nucleic acid amplification-based assay. For example, it can accept a competitor's primer set and determine the following information: (1) How it compares to the primers of the invention (e.g., overall rank, PCR and conservation ranking, etc.); (2) How it aligns to the exclude libraries (e.g., assessing cross-hybridization)—also used to compare primer and probe sets to newly published sequences; and (3) If the sequence has been previously published. This step requires keeping a database of sequences published in scientific journals, posters, and other presentations.

Example 3

Multiplexing

The Exclude/Include capability is ideally suited for designing multiplex reactions. The parameters for designing multiple primer and probe sets adhere to a more stringent set of parameters than those used for the initial Exclude/Include function. Each set of primers and probe, together with the resulting amplicon, is screened against the other sets that constitute the multiplex reaction. As new targets are accepted, their sequences are automatically added to the Exclude category.

The database is designed to interrogate the online databases to determine and acquire, if necessary, any new sequences relevant to the targets. These sequences are evaluated against the optimal primer/probe set. If they represent a new genotype or strain, then a multiple sequence alignment may be required.

Example 4

Sequences Identified for Detecting influenza A, influenza B, 2009 influenza A/H1N1, oseltamivir resistant and/or oseltamivir sensitive 2009 influenza A/H1N1

The set of primers and probes were then scored according to the methods described herein to identify the optimized primers and probes of Table 4. It should be noted that the primers, as they are sequences that anneal to a plurality of all identified or unidentified influenza A, influenza B and 2009 influenza A/H1N1, can also be used as probes either in the presence or absence of amplification of a sample.

TABLE 4

Optimized Primers and Probes for the Detection of influenza A, influenza B, 2009 influenza A/H1N1, oseltamivir-resistant influenza A/H1N1, oseltamivir-sensitive 2009 influenza A/H1N1, Process Control, 2009 influenza A/H3N2

| Group No. | Forward Primer | Probe | Reverse Primer |
|---|---|---|---|
| | | Influenza A | |
| 1 | GCTCTCATGGAATGGCTAAAGAC SEQ ID NO: 1 | TCACCGTGCCCAGTGAGCGAG SEQ ID NO: 2 | GCATTTTGGACAAAGCGTCTACG SEQ ID NO: 3 |
| | | Influenza B | |
| 2 | TGGATACAAGTCCTTATCAACTCTG SEQ ID NO: 4 GTTGCTAAACTTGTTGCTACTGA SEQ ID NO: 7 | TCGAAGAGTGAGTTGAGGATCCG SEQ ID NO: 5 TTGAGGATCCGATGGCCATCTT SEQ ID NO: 8 | TGCTCTTGACCAAATTGGGAT SEQ ID NO: 6 GCTGCTCGAATTGGCTTT SEQ ID NO: 9 |

TABLE 4-continued

Optimized Primers and Probes for the Detection of influenza A, influenza B, 2009
influenza A/H1N1, oseltamivir-resistant influenza A/H1N1, oseltamivir-sensitive
2009 influenza A/H1N1, Process Control, 2009 influenza A/H3N2

| Group No. | Forward Primer | Probe | Reverse Primer |
|---|---|---|---|
| 3 | TGGATACAAGTCCTTATCAACTCTG SEQ ID NO: 4 GCTAAACTTGTTGCTACTGATGA SEQ ID NO: 11 | TCGAAGAGTGAGTTGAGGATCCG SEQ ID NO: 5 TTGAGGATCCGATGGCCATCTT SEQ ID NO: 8 | TGGTGATAATCGGTGCTCTTG SEQ ID NO: 10 GCTGCTCGAATTGGCTTT SEQ ID NO: 9 |
| 4 | TGGATACAAGTCCTTATCAACTCTG SEQ ID NO: 4 GCTAAACTTGTTGCTACTGATGA SEQ ID NO: 11 | TCGAAGAGTGAGTTGAGGATCCG SEQ ID NO: 5 TTGAGGATCCGATGGCCATCTT SEQ ID NO: 8 | TGCTCTTGACCAAATTGGGAT SEQ ID NO: 6 GCTGCTCGAATTGGCTTT SEQ ID NO: 9 |
| 5 | TGGATACAAGTCCTTATCAACTCTG SEQ ID NO: 4 GTTGCTAAACTTGTTGCTACTGA SEQ ID NO: 7 | TCGAAGAGTGAGTTGAGGATCCG SEQ ID NO: 5 TTGAGGATCCGATGGCCATCTT SEQ ID NO: 8 | TGGTGATAACGGTGCTCTTG SEQ ID NO: 10 GCTGCTCGAATTGGCTTT SEQ ID NO: 9 |
| 6 | TGGATACAAGTCCTTATCAACTCTG SEQ ID NO: 4 GTTGCTAAACTTGTTGCTACTGA SEQ ID NO: 7 | TCGAAGAGTGAGTTGAGGATCCG SEQ ID NO: 5 TTGAGGATCCGATGGCCATCTT SEQ ID NO: 8 | TCGGTGCTCTTGACCAAATT SEQ ID NO: 12 GCTGCTCGAATTGGCTTT SEQ ID NO: 9 |
| 7 | TACAAGTCCTTATCAACTCTGCAT SEQ ID NO: 13 GTTGCTAAACTTGTTGCTACTGA SEQ ID NO: 7 | TCGAAGAGTGAGTTGAGGATCCG SEQ ID NO: 5 TTGAGGATCCGATGGCCATCTT SEQ ID NO: 8 | TGGTGATAATCGGTGCTCTTG SEQ ID NO: 10 GCTGCTCGAATTGGCTTT SEQ ID NO: 9 |
| 8 | CTTGTTGCTAAACTTGTTGC SEQ ID NO: 14 | TCGGATCCTCAACTCACTCTTCG SEQ ID NO: 15 TCGGATCCTCAATTCACTCTTCG SEQ ID NO: 17 | TCAGCTGCTCGAATTG SEQ ID NO: 16 TTTCAGCTGCTCGAATTG SEQ ID NO: 18 |
| 9 | TGGATACAAGTCCTTATCAACTCTG SEQ ID NO: 4 GTTGCTAAACTTGTTGCTACTGA SEQ ID NO: 7 | TTGAGGATCCGATGGCCATCTT SEQ ID NO: 8 | GCTGCTCGAATTGGCTTT SEQ ID NO: 9 |
| 10 | CATCGGATCCTCAATTCACTCTTCG SEQ ID NO: 19 | AATGAAGGACATTCAAAGCCAAT TCGAGCAGCTGA SEQ ID NO: 20 | CTTGACCAAATTGGGATAAGACTCC SEQ ID NO: 21 |
| 11 | CATCGGATCCTCAATTCACTCTTCG SEQ ID NO: 19 | CAAAGCCAATTCGAGCAGCTGAA ACTGC SEQ ID NO: 22 | CTTGACCAAATTGGGATAAGACTCC SEQ ID NO: 21 |
| 12 | CATCGGATCCTCAATTCACTCTTCG SEQ ID NO: 19 | CAAAGCCAATTCGAGCAGCTGAA ACTGC SEQ ID NO: 22 | GTGATAATCGGTGCTCTTGACCAAA SEQ ID NO: 23 |
| 13 | CATCGGATCCTCAATTCACTCTTCG SEQ ID NO: 19 | AATGAAGGACATTCAAAGCCAAT TCGAG SEQ ID NO: 20 | GTGATAATCGGTGCTCTTGACCAAA SEQ ID NO: 23 |
| 14 | AACATGACCACAACACAAATTGAGG SEQ ID NO: 24 TCACAACACAAATTGAGGTGGGT SEQ ID NO: 27 | TCCTGCTTCAAAGTTTATAGTGG CATTGGTTGCTC SEQ ID NO: 25 | GTAATCAAGGGCTCTTTGCCATGAA SEQ ID NO: 26 TTGGCCAGGGTAGTCAAGGG SEQ ID NO: 28 |
| 15 | AACATGACCACAACACAAATTGAGG SEQ ID NO: 24 TCACAACACAAATTGAGGTGGGT SEQ ID NO: 27 | TCCTGCTTCAAAGTTTATAGTGG CATTGGTTGCTC SEQ ID NO: 25 | CTGTTTAGGCGGTTTTGACCAG SEQ ID NO: 29 GTAATCAAGGGCTCTTTGCCATGAA SEQ ID NO: 26 |
| 2009 Influenza A/H1N1 (SoIV) | | | |
| 16 | GCTAGTTAAAAAAGGAAATTCATACC SEQ ID NO: 30 TGGAGCAAAAAGCTTCTACAAAAA SEQ ID NO: 33 | CAGCAAATCCTACATTAATGATA AAGGGA SEQ ID NO: 31 | TGGTCAGCACTAGTAGATGGA SEQ ID NO: 32 CATATGCATCTGCATTCTGATAGA SEQ ID NO: 34 |
| 17 | GCTAGTTAAAAAAGGAAATTCATACC SEQ ID NO: 30 TGGAGCAAAAAGCTTCTACAAAAA SEQ ID NO: 33 | CAGCAAATCCTACATTAATGATA AAGGGA SEQ ID NO: 31 | TTTGTTGGTCAGCACTAGTAGAT SEQ ID NO: 35 CATATGCATCTGCATTCTGATAGA SEQ ID NO: 34 |

TABLE 4-continued

Optimized Primers and Probes for the Detection of influenza A, influenza B, 2009 influenza A/H1N1, oseltamivir-resistant influenza A/H1N1, oseltamivir-sensitive 2009 influenza A/H1N1, Process Control, 2009 influenza A/H3N2

| Group No. | Forward Primer | Probe | Reverse Primer |
|---|---|---|---|
| 18 | GATAGTCCCCAAGACAAGTTCATGG<br>SEQ ID NO: 36<br><br>CAAGTTCATGGCCCAATCATGACT<br>SEQ ID NO: 39 | CATTAATGTAGGATTTGCTGAGC<br>TTTGGG<br>SEQ ID NO: 37<br>ACAAAGGTGTAACGGCAGCATGT<br>CC<br>SEQ ID NO: 40 | GATGGTGAATGCCCCATAGCAC<br>SEQ ID NO: 38<br><br>CACTAGAAGATGGATGGTGAATGCC<br>SEQ ID NO: 41 |
| 19 | AAAGGGAAAGAAGTTCTCGTGCTAT<br>SEQ ID NO: 42<br><br>TCATATCCAAAGCTCAGCAAATCCT<br>SEQ ID NO: 45 | ACTAGTAGATGGATGGTGAATGCC<br>CC<br>SEQ ID NO: 43<br>GCATTCTGATAGAGACTTTGTTGG<br>TCAGC<br>SEQ ID NO: 46 | GCTATTTCCGGCTTGAACTTCTT<br>SEQ ID NO: 44<br><br>GCTGTATCTTGATGTCCCCACAAAA<br>SEQ ID NO: 47 |
| | | Oseltamivir Resistance or Sensitivity | |
| 20 | GTCGAAATGAATGCCCCTAATTATC<br>SEQ ID NO: 48<br>GTCGAAATGAATGCCCCTAATTACC<br>SEQ ID NO: 51 | AGCCATGCCAGTTATCCCTGC<br>SEQ ID NO: 49 | CGTGGATTGTCTCCGAAA<br>SEQ ID NO: 50 |
| 21 | GTCGAAATGAATGCCCCTAATTATC<br>SEQ ID NO: 48<br>GTCGAAATGAATGCCCCTAATTACC<br>SEQ ID NO: 51<br>CGAAATGAATGCCCCTAATTATCAC<br>SEQ ID NO: 52 | AGCCATGCCAGTTATCCCTGC<br>SEQ ID NO: 49 | CGTGGATTGTCTCCGAAA<br>SEQ ID NO: 50 |
| 22 | CGAAATGAATGCCCCTAATTATCAC<br>SEQ ID NO: 52 | AGCCATGCCAGTTATCCCTGC<br>SEQ ID NO: 49 | CGTGGATTGTCTCCGAAA<br>SEQ ID NO: 50 |
| 23 | TGTGCATGTGTAAATGGTTC<br>SEQ ID NO: 53 | AGCATTCCTCATAGTGAT<br>SEQ ID NO: 54<br>AATGCCCCTAATTATAC<br>SEQ ID NO: 56 | GAATCAGGATAACAGGAGCAT<br>SEQ ID NO: 55 |
| 24 | CTTCAGAATAGAAAAGGGAAAGATA<br>GTC<br>SEQ ID NO: 57 | TTGGCGTTTCATAGTAATAATTAG<br>GGGATTAACGCCAA<br>SEQ ID NO: 58<br>AACCGCAACCCTAATTATCACTAT<br>GAGGAATTGCGGTT<br>SEQ ID NO: 60 | TTCGAGCCATGCCAGTT<br>SEQ ID NO: 59 |
| 25 | TCATACAAGATCTTCAGAATAGAAA<br>AGG<br>SEQ ID NO: 61 | TTGGCGTTTCATAGTAATAATTAG<br>GGGATTAACGCCAA<br>SEQ ID NO: 58<br>AACCGCAACCCTAATTATCACTAT<br>GAGGAATTGCGGTT<br>SEQ ID NO: 60 | ATTTCACTAGAATCAGGATAACAGG<br>AG<br>SEQ ID NO: 62 |
| 26 | CTTCAGAATAGAAAAGGGAAAGATA<br>GTC<br>SEQ ID NO: 57 | AACCGCAACCCTAATTATTACTAT<br>GAGGAATTGCGGTT<br>SEQ ID NO: 63<br>AACCGCAACCCTAATTATCACTAT<br>GAGGAATTGCGGTT<br>SEQ ID NO: 60 | TTCGAGCCATGCCAGTT<br>SEQ ID NO: 59 |
| 27 | TCATACAAGATCTTCAGAATAGAAAA<br>GG<br>SEQ ID NO: 61 | AACCGCAACCCTAATTATTACTAT<br>GAGGAATTGCGGTT<br>SEQ ID NO: 63<br>AACCGCAACCCTAATTATCACTAT<br>GAGGAATTGCGGTT<br>SEQ ID NO: 60 | ATTTCACTAGAATCAGGATAACAGG<br>AG<br>SEQ ID NO: 62 |
| 28 | CTTCAGAATAGAAAAGGGAAAGATAG<br>TC<br>SEQ ID NO: 57 | ATTCCTCATAGTAATAATTAGGGG<br>SEQ ID NO: 64<br>ATTCCTCATAGTGATAATTAGGGG<br>SEQ ID NO: 65 | TTCGAGCCATGCCAGTT<br>SEQ ID NO: 59 |

TABLE 4-continued

Optimized Primers and Probes for the Detection of influenza A, influenza B, 2009 influenza A/H1N1, oseltamivir-resistant influenza A/H1N1, oseltamivir-sensitive 2009 influenza A/H1N1, Process Control, 2009 influenza A/H3N2

| Group No. | Forward Primer | Probe | Reverse Primer |
|---|---|---|---|
| 29 | CTTCAGAATAGAAAAGGGAAAGATAGTC<br>SEQ ID NO: 57 | ATTCCTCATAGTGATAATTAGG<br>SEQ ID NO: 66<br>ATTCCTCATAGTAATAATTAGGG<br>SEQ ID NO: 67 | TTCGAGCCATGCCAGTT<br>SEQ ID NO: 59 |
| | | Process Control | |
| 30 | CAATGCAACGTTCTCCAAC<br>SEQ ID NO: 68 | TGCAGGATGCAGCGCCTTAC<br>SEQ ID NO: 69 | TAACGGTTGCTTGTTCAGC<br>SEQ ID NO: 70 |
| 31 | AATCTTCGTAAAACGTTCGTGTC<br>SEQ ID NO: 71 | CACTTTTACCGTGGTGTCGATGTCAAAC<br>SEQ ID NO: 72 | CGAAGAGATTGTCAACAGGT<br>SEQ ID NO: 73 |
| 32 | GTCCGAGACCAATGTGC<br>SEQ ID NO: 74 | CCGTTCCCTACAACGAGCCTAAATTCATA<br>SEQ ID NO: 75 | CAGGCAGCCCGATCTATT<br>SEQ ID NO: 76 |
| | | 2009 Influenza A/H3N2 | |
| 33 | TATGCCCCAAACTAGCAGAATACA<br>SEQ ID NO: 77<br>TGGTCAAAGCCGCAATGT<br>SEQ ID NO: 89 | CCACCAGCGGAAAGCC<br>SEQ ID NO: 101<br>CTTGTCACCCAGATGTCCCC<br>SEQ ID NO: 113 | TCGCATGACACATAAGGTTCT<br>SEQ ID NO: 124<br>TTGTTTAGTGTTGTTCCCTGTC<br>SEQ ID NO: 136 |
| 34 | TATGCCCCAAACTAGCAGAATACA<br>SEQ ID NO: 78<br>TGGTCAAAGCCGCAATG<br>SEQ ID NO: 90 | CCACCAGCGGAAAGCC<br>SEQ ID NO: 102<br>CTTGTCACCCAGATGTCCCC<br>SEQ ID NO: 114 | TCGCATGACACATAAGGTTCT<br>SEQ ID NO: 125<br>TTGTTTAGTGTTGTTCCCTGTC<br>SEQ ID NO: 137 |
| 35 | GTATCTGACCAACACCACCAT<br>SEQ ID NO: 79<br>GCTGTGTGAACCAACAATAATAGA<br>SEQ ID NO: 91 | CCACCAGCGGAAAGCC<br>SEQ ID NO: 103<br>AGAGAAGGAAATATGCCCCAAACT<br>SEQ ID NO: 115 | TGTCACCCAGATGTCC<br>SEQ ID NO: 126<br>TCGCATGACACATAAGGTTCTC<br>SEQ ID NO: 138 |
| 36 | GCTGTGTGAACCAACAATAATAGAA<br>SEQ ID NO: 80<br>GTATCTGACCAACACCACCAT<br>SEQ ID NO: 92 | CCACCAGCGGAAAGCC<br>SEQ ID NO: 104<br>AGAGAAGGAAATATGCCCCAAACT<br>SEQ ID NO: 116 | TGTCACCCAGATGTCC<br>SEQ ID NO: 127<br>TCGCATGACACATAAGGTTCTC<br>SEQ ID NO: 139 |
| 37 | ACAGAGATAGTGTATCTGACCAAC<br>SEQ ID NO: 81<br>GCTGTGTGAACCAACAATAATAGA<br>SEQ ID NO: 93 | CCACCAGCGGAAAGCC<br>SEQ ID NO: 105<br>CCACCATAGAGAAGGAAATATGCCCAAACT<br>SEQ ID NO: 117 | TGTCACCCAGATGTCC<br>SEQ ID NO: 128<br>TCGCATGACACATAAGGTTCTC<br>SEQ ID NO: 140 |
| 38 | TGCTGTGTGAACCAACAATAATAGA<br>SEQ ID NO: 82<br>GTATCTGACCAACACCACCAT<br>SEQ ID NO: 94 | CCACCAGCGGAAAGCC<br>SEQ ID NO: 106<br>AGAGAAGGAAATATGCCCCAAACT<br>SEQ ID NO: 118 | TGTCACCCAGATGTCC<br>SEQ ID NO: 129<br>TCGCATGACACATAAGGTTCTC<br>SEQ ID NO: 141 |
| 39 | ACAGAGATAGTGTATCTGACCAAC<br>SEQ ID NO: 83<br>GCTGTGTGAACCAACAATAATAGAA<br>SEQ ID NO: 95 | CCACCAGCGGAAAGCC<br>SEQ ID NO: 107<br>CCACCATAGAGAAGGAAATATGCCCAAACT<br>SEQ ID NO: 119 | TGTCACCCAGATGTCC<br>SEQ ID NO: 130<br>TCGCATGACACATAAGGTTCTC<br>SEQ ID NO: 142 |
| 40 | ACAGAGATAGTGTATCTGACCAAC<br>SEQ ID NO: 84<br>TGCTGTGTGAACCAACAATAATAGA<br>SEQ ID NO: 96 | CCACCAGCGGAAAGCC<br>SEQ ID NO: 108<br>CCACCATAGAGAAGGAAATATGCCCAAACT<br>SEQ ID NO: 120 | TGTCACCCAGATGTCC<br>SEQ ID NO: 131<br>TCGCATGACACATAAGGTTCTC<br>SEQ ID NO: 143 |
| 41 | TGCTGTGTGAACCAACAATAATAG<br>SEQ ID NO: 85<br>GTATCTGACCAACACCACCAT<br>SEQ ID NO: 97 | CCACCAGCGGAAAGCC<br>SEQ ID NO: 109<br>AGAGAAGGAAATATGCCCCAAACT<br>SEQ ID NO: 121 | TGTCACCCAGATGTCC<br>SEQ ID NO: 132<br>TCGCATGACACATAAGGTTCTC<br>SEQ ID NO: 144 |
| 42 | TGACCAACACCACCAT<br>SEQ ID NO: 86<br>TGCTGTGTGAACCAACAATAATAGA<br>SEQ ID NO: 98 | CCACCAGCGGAAAGCC<br>SEQ ID NO: 110<br>AGAGAAGGAAATATGCCCCAAACT<br>SEQ ID NO: 122 | TGTCACCCAGATGTCC<br>SEQ ID NO: 133<br>TCGCATGACACATAAGGTTCTC<br>SEQ ID NO: 145 |

TABLE 4-continued

Optimized Primers and Probes for the Detection of influenza A, influenza B, 2009 influenza A/H1N1, oseltamivir-resistant influenza A/H1N1, oseltamivir-sensitive 2009 influenza A/H1N1, Process Control, 2009 influenza A/H3N2

| Group No. | Forward Primer | Probe | Reverse Primer |
|---|---|---|---|
| 43 | ACAGAGATAGTGTATCTGACCAAC<br>SEQ ID NO: 87<br><br>TGCTGTGTGAACCAACAATAATAG<br>SEQ ID NO: 99 | CCACCAGCGGAAAGCC<br>SEQ ID NO: 111<br><br>CCACCATAGAGAAGGAAATATGCC<br>CCAAACT<br>SEQ ID NO: 123 | TGTCACCCAGATGTCC<br>SEQ ID NO: 134<br><br>TCGCATGACACATAAGGTTCTC<br>SEQ ID NO: 146 |
| 44 | GGCAAAGCTGCATCAAT<br>SEQ ID NO: 88<br><br>GGTGCTTTTATGTGGAGTTGATAAG<br>SEQ ID NO: 100 | TATGTACCTGAGGTGCCACAAAAC<br>ACAACAATAC<br>SEQ ID NO: 112 | TCGATGTCCGCCCCAT<br>SEQ ID NO: 135<br><br>GCCATGAGCCTGTTCCA<br>SEQ ID NO: 147 |
| 45 | GACTGCTAGCTTCATTTACAATGG<br>SEQ ID NO: 148 | TTTTGGACCATGAAACAATACTAT<br>CTACAAGCCTC<br>SEQ ID NO: 219 | GCATTCTGACTCCTGGGT<br>SEQ ID NO: 290 |
| 46 | AACTGCTAGCTTCATTTACAATGG<br>SEQ ID NO: 149 | TTTTGGACCATGAAACAATACTAT<br>CTACAAGCCTC<br>SEQ ID NO: 220 | GCATTCTGACTCCTGGGT<br>SEQ ID NO: 291 |
| 47 | CTACTGCTAGCTTCATTTACAATGG<br>SEQ ID NO: 150 | TTTTGGACCATGAAACAATACTAT<br>CTACAAGCCTC<br>SEQ ID NO: 221 | GCATTCTGACTCCTGGGT<br>SEQ ID NO: 292 |
| 48 | GACTGCTAGCTTCATTTACAATGG<br>SEQ ID NO: 151 | TTTTGGACCATGAAACAATACTAT<br>CTACAAGCCTC<br>SEQ ID NO: 222 | GTCATTACTACTGTACAAGTTCCAT<br>SEQ ID NO: 293 |
| 49 | AACTGCTAGCTTCATTTACAATGG<br>SEQ ID NO: 152 | TTTTGGACCATGAAACAATACTAT<br>CTACAAGCCTC<br>SEQ ID NO: 223 | GTCATTACTACTGTACAAGTTCCAT<br>SEQ ID NO: 294 |
| 50 | CTACTGCTAGCTTCATTTACAATGG<br>SEQ ID NO: 153 | TTTTGGACCATGAAACAATACTAT<br>CTACAAGCCTC<br>SEQ ID NO: 224 | GTCATTACTACTGTACAAGTTCCAT<br>SEQ ID NO: 295 |
| 51 | GACTGCTAGCTTCATTTACAATGG<br>SEQ ID NO: 154 | TTTTGGACCATGAAACAATACTAT<br>CTACAAGCCT<br>SEQ ID NO: 225 | GCATTCTGACTCCTGGGT<br>SEQ ID NO: 296 |
| 52 | AACTGCTAGCTTCATTTACAATGG<br>SEQ ID NO: 155 | TTTTGGACCATGAAACAATACTAT<br>CTACAAGCCT<br>SEQ ID NO: 226 | GCATTCTGACTCCTGGGT<br>SEQ ID NO: 297 |
| 53 | CTACTGCTAGCTTCATTTACAATGG<br>SEQ ID NO: 156 | TTTTGGACCATGAAACAATACTAT<br>CTACAAGCCT<br>SEQ ID NO: 227 | GCATTCTGACTCCTGGGT<br>SEQ ID NO: 298 |
| 54 | GACTGCTAGCTTCATTTACAATGG<br>SEQ ID NO: 157 | TTTTGGACCATGAAACAATACTAT<br>CTACAAGCCT<br>SEQ ID NO: 228 | GTCATTACTACTGTACAAGTTCCAT<br>SEQ ID NO: 299 |
| 55 | AACTGCTAGCTTCATTTACAATGG<br>SEQ ID NO: 158 | TTTTGGACCATGAAACAATACTAT<br>CTACAAGCCT<br>SEQ ID NO: 229 | GTCATTACTACTGTACAAGTTCCAT<br>SEQ ID NO: 300 |
| 56 | CTACTGCTAGCTTCATTTACAATGG<br>SEQ ID NO: 159 | TTTTGGACCATGAAACAATACTAT<br>CTACAAGCCT<br>SEQ ID NO: 230 | GTCATTACTACTGTACAAGTTCCAT<br>SEQ ID NO: 301 |
| 57 | GACTGCTAGCTTCATTTACAATGG<br>SEQ ID NO: 160 | TTCTTTGGACCATGAAACAATACT<br>ATCTACAAGCC<br>SEQ ID NO: 231 | GCATTCTGACTCCTGGGT<br>SEQ ID NO: 302 |
| 58 | AACTGCTAGCTTCATTTACAATGG<br>SEQ ID NO: 161 | TTCTTTGGACCATGAAACAATACT<br>ATCTACAAGCC<br>SEQ ID NO: 232 | GCATTCTGACTCCTGGGT<br>SEQ ID NO: 303 |
| 59 | CTACTGCTAGCTTCATTTACAATGG<br>SEQ ID NO: 162 | TTCTTTGGACCATGAAACAATACT<br>ATCTACAAGCC<br>SEQ ID NO: 233 | GCATTCTGACTCCTGGGT<br>SEQ ID NO: 304 |

TABLE 4-continued

Optimized Primers and Probes for the Detection of influenza A, influenza B, 2009 influenza A/H1N1, oseltamivir-resistant influenza A/H1N1, oseltamivir-sensitive 2009 influenza A/H1N1, Process Control, 2009 influenza A/H3N2

| Group No. | Forward Primer | Probe | Reverse Primer |
|---|---|---|---|
| 60 | GACTGCTAGCTTCATTTACAATGG<br>SEQ ID NO: 163 | TTCTTTGGACCATGAAACAATACT<br>ATCTACAAGCC<br>SEQ ID NO: 234 | CAAGTTCCATTGATACAAACGCA<br>SEQ ID NO: 305 |
| 61 | AACTGCTAGCTTCATTTACAATGG<br>SEQ ID NO: 164 | TTCTTTGGACCATGAAACAATACT<br>ATCTACAAGCC<br>SEQ ID NO: 235 | CAAGTTCCATTGATACAAACGCA<br>SEQ ID NO: 306 |
| 62 | CTACTGCTAGCTTCATTTACAATGG<br>SEQ ID NO: 165 | TTCTTTGGACCATGAAACAATACT<br>ATCTACAAGCC<br>SEQ ID NO: 236 | CAAGTTCCATTGATACAAACGCA<br>SEQ ID NO: 307 |
| 63 | GACTGCTAGCTTCATTTACAATGG<br>SEQ ID NO: 165 | TTCTTTGGACCATGAAACAATACT<br>ATCTACAAGCC<br>SEQ ID NO: 237 | GTCATTACTACTGTACAAGTTCCAT<br>SEQ ID NO: 308 |
| 64 | AACTGCTAGCTTCATTTACAATGG<br>SEQ ID NO: 167 | TTCTTTGGACCATGAAACAATACT<br>ATCTACAAGCC<br>SEQ ID NO: 238 | GTCATTACTACTGTACAAGTTCCAT<br>SEQ ID NO: 309 |
| 65 | CTACTGCTAGCTTCATTTACAATGG<br>SEQ ID NO: 168 | TTCTTTGGACCATGAAACAATACT<br>ATCTACAAGCC<br>SEQ ID NO: 239 | GTCATTACTACTGTACAAGTTCCAT<br>SEQ ID NO: 310 |
| 66 | AACTGCTAGCTTCATTTACAATGG<br>SEQ ID NO: 169 | TTCTTTGGACCATGAAACAATACT<br>ATCTACAAGCA<br>SEQ ID NO: 240 | GTCATTACTACTGTACAAGTTCCAT<br>SEQ ID NO: 311 |
| 67 | GACTGCTAGCTTCATTTACAATGG<br>SEQ ID NO: 170 | TTCTTTGGACCATGAAACAATACT<br>ATCTACAAGCA<br>SEQ ID NO: 241 | GTCATTACTACTGTACAAGTTCCAT<br>SEQ ID NO: 312 |
| 68 | CTACTGCTAGCTTCATTTACAATGG<br>SEQ ID NO: 171 | TTCTTTGGACCATGAAACAATACT<br>ATCTACAAGCA<br>SEQ ID NO: 242 | GTCATTACTACTGTACAAGTTCCAT<br>SEQ ID NO: 313 |
| 69 | GACTGCTAGCTTCATTTACAATGG<br>SEQ ID NO: 172 | TCTTTGGACCATGAAACAATACTA<br>TCTACAAGCCT<br>SEQ ID NO: 243 | CAAGTTCCATTGATACAAACGCA<br>SEQ ID NO: 314 |
| 70 | AACTGCTAGCTTCATTTACAATGG<br>SEQ ID NO: 173 | TCTTTGGACCATGAAACAATACTA<br>TCTACAAGCCT<br>SEQ ID NO: 244 | CAAGTTCCATTGATACAAACGCA<br>SEQ ID NO: 315 |
| 71 | CTACTGCTAGCTTCATTTACAATGG<br>SEQ ID NO: 174 | TCTTTGGACCATGAAACAATACTA<br>TCTACAAGCCT<br>SEQ ID NO: 245 | CAAGTTCCATTGATACAAACGCA<br>SEQ ID NO: 316 |
| 72 | AACTGCTAGCTTCATTTACAATGG<br>SEQ ID NO: 175 | TCTTTGGACCATGAAACAATACTA<br>TCTACAAGCCT<br>SEQ ID NO: 246 | GTCATTACTACTGTACAAGTTCCAT<br>SEQ ID NO: 317 |
| 73 | GACTGCTAGCTTCATTTACAATGG<br>SEQ ID NO: 176 | TCTTTGGACCATGAAACAATACTA<br>TCTACAAGCCT<br>SEQ ID NO: 247 | GTCATTACTACTGTACAAGTTCCAT<br>SEQ ID NO: 318 |
| 74 | CTACTGCTAGCTTCATTTACAATGG<br>SEQ ID NO: 177 | TCTTTGGACAATGAAACAATACTA<br>TCTACAAGCCT<br>SEQ ID NO: 248 | GTCATTACTACTGTACAAGTTCCAT<br>SEQ ID NO: 319 |
| 75 | AACTGCTAGCTTCATTTACAATGG<br>SEQ ID NO: 178 | TACAAATGCATTCTGACTCCTGGG<br>TCCTGA<br>SEQ ID NO: 249 | GTCATTACTACTGTACAAGTTCCAT<br>SEQ ID NO: 320 |
| 76 | GACTGCTAGCTTCATTTACAATGG<br>SEQ ID NO: 179 | TACAAATGCATTCTGACTCCTGGG<br>TCCTGA<br>SEQ ID NO: 250 | GTCATTACTACTGTACAAGTTCCAT<br>SEQ ID NO: 321 |
| 77 | CTACTGCTAGCTTCATTTACAATGG<br>SEQ ID NO: 180 | TACAAATGCATTCTGACTCCTGGG<br>TCCTGA<br>SEQ ID NO: 251 | GTCATTACTACTGTACAAGTTCCAT<br>SEQ ID NO: 322 |

TABLE 4-continued

Optimized Primers and Probes for the Detection of influenza A, influenza B, 2009 influenza A/H1N1, oseltamivir-resistant influenza A/H1N1, oseltamivir-sensitive 2009 influenza A/H1N1, Process Control, 2009 influenza A/H3N2

| Group No. | Forward Primer | Probe | Reverse Primer |
|---|---|---|---|
| 78 | GACTGCTAGCTTCATTTACAATGG SEQ ID NO: 181 | TACAAATGCATTCTGACTCCTGGG TCCTG SEQ ID NO: 252 | GTCATTACTACTGTACAAGTTCCAT SEQ ID NO: 323 |
| 79 | AACTGCTAGCTTCATTTACAATGG SEQ ID NO: 182 | TACAAATGCATTCTGACTCCTGGG TCCTG SEQ ID NO: 253 | GTCATTACTACTGTACAAGTTCCAT SEQ ID NO: 324 |
| 80 | CTACTGCTAGCTTCATTTACAATGG SEQ ID NO: 183 | TACAAATGCATTCTGACTCCTGGG TCCTG SEQ ID NO: 254 | GTCATTACTACTGTACAAGTTCCAT SEQ ID NO: 325 |
| 81 | AACTGCTAGCTTCATTTACAATGG SEQ ID NO: 184 | CTTTGGACCATGAAACAATACTAT CTACAAGCATC SEQ ID NO: 255 | GTCATTACTACTGTACAAGTTCCAT SEQ ID NO: 326 |
| 82 | GACTGCTAGCTTCATTTACAATGG SEQ ID NO: 185 | CTTTGGACCATGAAACAATACTAT CTACAAGCATC SEQ ID NO: 256 | GTCATTACTACTGTACAAGTTCCAT SEQ ID NO: 327 |
| 83 | CTACTGCTAGCTTCATTTACAATGG SEQ ID NO: 186 | CTTTGGACCATGAAACAATACTAT CTACAAGCATC SEQ ID NO: 257 | GTCATTACTACTGTACAAGTTCCAT SEQ ID NO: 328 |
| 84 | AACTGCTAGCTTCATTTACAATGG SEQ ID NO: 187 | CGCATTCTGACTCCTGGGTCCTGA SEQ ID NO: 258 | GTCATTACTACTGTACAAGTTCCAT SEQ ID NO: 329 |
| 85 | GACTGCTAGCTTCATTTACAATGG SEQ ID NO: 188 | CGCATTCTGACTCCTGGGTCCTGA SEQ ID NO: 259 | GTCATTACTACTGTACAAGTTCCAT SEQ ID NO: 330 |
| 86 | CTACTGCTAGCTTCATTTACAATGG SEQ ID NO: 189 | CGCATTCTGACTCCTGGGTCCTGA SEQ ID NO: 260 | GTCATTACTACTGTACAAGTTCCAT SEQ ID NO: 331 |
| 87 | AACTGCTAGCTTCATTTACAATGG SEQ ID NO: 190 | CGCATTCTGACTCCTGGGTCCTG SEQ ID NO: 261 | GTCATTACTACTGTACAAGTTCCAT SEQ ID NO: 332 |
| 88 | GACTGCTAGCTTCATTTACAATGG SEQ ID NO: 191 | CGCATTCTGACTCCTGGGTCCTG SEQ ID NO: 262 | GTCATTACTACTGTACAAGTTCCAT SEQ ID NO: 333 |
| 89 | CTACTGCTAGCTTCATTTACAATGG SEQ ID NO: 192 | CGCATTCTGACTCCTGGGTCCTG SEQ ID NO: 263 | GTCATTACTACTGTACAAGTTCCAT SEQ ID NO: 334 |
| 90 | GACTGCTAGCTTCATTTACAATGG SEQ ID NO: 193 | CGCATTCTGACTCCTGGGTCCT SEQ ID NO: 264 | GTCATTACTACTGTACAAGTTCCAT SEQ ID NO: 335 |
| 91 | AACTGCTAGCTTCATTTACAATGG SEQ ID NO: 194 | CGCATTCTGACTCCTGGGTCCT SEQ ID NO: 265 | GTCATTACTACTGTACAAGTTCCAT SEQ ID NO: 336 |
| 92 | CTACTGCTAGCTTCATTTACAATGG SEQ ID NO: 195 | CGCATTCTGACTCCTGGGTCCT SEQ ID NO: 266 | GTCATTACTACTGTACAAGTTCCAT SEQ ID NO: 337 |
| 93 | GACTGCTAGCTTCATTTACAATGG SEQ ID NO: 196 | CATTCTGACTCCTGGGTCCTGAGG ATA SEQ ID NO: 267 | GTCATTACTACTGTACAAGTTCCAT SEQ ID NO: 338 |
| 94 | AACTGCTAGCTTCATTTACAATGG SEQ ID NO: 197 | CATTCTGACTCCTGGGTCCTGAGG ATA SEQ ID NO: 268 | GTCATTACTACTGTACAAGTTCCAT SEQ ID NO: 339 |
| 95 | CTACTGCTAGCTTCATTTACAATGG SEQ ID NO: 198 | CATTCTGACTCCTGGGTCCTGAGG ATA SEQ ID NO: 269 | GTCATTACTACTGTACAAGTTCCAT SEQ ID NO: 340 |
| 96 | CTACTGCTAGCTTCATTTACAATGG SEQ ID NO: 199 | AGCTTGTAGATAGTATTGTTTCAT GGTCCAAAGAA SEQ ID NO: 270 | GCATTCTGACTCCTGGGT SEQ ID NO: 341 |
| 97 | CTACTGCTAGCTTCATTTACAATGG SEQ ID NO: 200 | AGCTTGTAGATAGTATTGTTTCAT GGTCCAAAGAA SEQ ID NO: 271 | TGCATTCTGACTCCTGGGT SEQ ID NO: 342 |

TABLE 4-continued

Optimized Primers and Probes for the Detection of influenza A, influenza B, 2009 influenza A/H1N1, oseltamivir-resistant influenza A/H1N1, oseltamivir-sensitive 2009 influenza A/H1N1, Process Control, 2009 influenza A/H3N2

| Group No. | Forward Primer | Probe | Reverse Primer |
|---|---|---|---|
| 98 | CTACTGCTAGCTTCATTTACAATGG SEQ ID NO: 201 | AGCTTGTAGATAGTATTGTTTCATGGTCCAAAGAA SEQ ID NO: 272 | CAAGTTCCATTGATACAAACGCA SEQ ID NO: 343 |
| 99 | CTACTGCTAGCTTCATTTACAATGG SEQ ID NO: 202 | AGCTTGTAGATAGTATTGTTTCATGGTCCAAAGAA SEQ ID NO: 273 | TACAAGTTCCATTGATACAAACGCA SEQ ID NO: 344 |
| 100 | CTACTGCTAGCTTCATTTACAATGG SEQ ID NO: 203 | AGCTTGTAGATAGTATTGTTTCATGGTCCAAAGAA SEQ ID NO: 274 | GTCATTACTACTGTACAAGTTCCAT SEQ ID NO: 345 |
| 101 | GACTGCTAGCTTCATTTACAATGG SEQ ID NO: 204 | AAGGCTTGTAGATAGTATTGTTTCATGGTCCAAAG SEQ ID NO: 275 | GCATTCTGACTCCTGGGT SEQ ID NO: 346 |
| 102 | AACTGCTAGCTTCATTTACAATGG SEQ ID NO: 205 | AAGGCTTGTAGATAGTATTGTTTCATGGTCCAAAG SEQ ID NO: 276 | GCATTCTGACTCCTGGGT SEQ ID NO: 347 |
| 103 | AACTGCTAGCTTCATTTACAATGG SEQ ID NO: 206 | AAGGCTTGTAGATAGTATTGTTTCATGGTCCAAAG SEQ ID NO: 277 | TGCATTCTGACTCCTGGGT SEQ ID NO: 348 |
| 104 | GACTGCTAGCTTCATTTACAATGG SEQ ID NO: 207 | AAGGCTTGTAGATAGTATTGTTTCATGGTCCAAAG SEQ ID NO: 278 | TGCATTCTGACTCCTGGGT SEQ ID NO: 349 |
| 105 | CTACTGCTAGCTTCATTTACAATGG SEQ ID NO: 208 | AAGGCTTGTAGATAGTATTGTTTCATGGTCCAAAG SEQ ID NO: 279 | GCATTCTGACTCCTGGGT SEQ ID NO: 350 |
| 106 | CTACTGCTAGCTTCATTTACAATGG SEQ ID NO: 209 | AAGGCTTGTAGATAGTATTGTTTCATGGTCCAAAG SEQ ID NO: 280 | TGCATTCTGACTCCTGGGT SEQ ID NO: 351 |
| 107 | GACTGCTAGCTTCATTTACAATGG SEQ ID NO: 210 | AAGGCTTGTAGATAGTATTGTTTCATGGTCCAAAG SEQ ID NO: 281 | CAAGTTCCATTGATACAAACGCA SEQ ID NO: 352 |
| 108 | AACTGCTAGCTTCATTTACAATGG SEQ ID NO: 211 | AAGGCTTGTAGATAGTATTGTTTCATGGTCCAAAG SEQ ID NO: 282 | CAAGTTCCATTGATACAAACGCA SEQ ID NO: 353 |
| 109 | CTACTGCTAGCTTCATTTACAATGG SEQ ID NO: 212 | AAGGCTTGTAGATAGTATTGTTTCATGGTCCAAAG SEQ ID NO: 283 | CAAGTTCCATTGATACAAACGCA SEQ ID NO: 354 |
| 110 | AACTGCTAGCTTCATTTACAATGG SEQ ID NO: 213 | AAGGCTTGTAGATAGTATTGTTTCATGGTCCAAAG SEQ ID NO: 284 | TACAAGTTCCATTGATACAAACGCA SEQ ID NO: 355 |
| 111 | GACTGCTAGCTTCATTTACAATGG SEQ ID NO: 214 | AAGGCTTGTAGATAGTATTGTTTCATGGTCCAAAG SEQ ID NO: 285 | TACAAGTTCCATTGATACAAACGCA SEQ ID NO: 356 |
| 112 | CTACTGCTAGCTTCATTTACAATGG SEQ ID NO: 215 | AAGGCTTGTAGATAGTATTGTTTCATGGTCCAAAG SEQ ID NO: 286 | TACAAGTTCCATTGATACAAACGCA SEQ ID NO: 357 |
| 113 | GACTGCTAGCTTCATTTACAATGG SEQ ID NO: 216 | AAGGCTTGTAGATAGTATTGTTTCATGGTCCAAAG SEQ ID NO: 287 | GTCATTACTACTGTACAAGTTCCAT SEQ ID NO: 358 |
| 114 | AACTGCTAGCTTCATTTACAATGG SEQ ID NO: 217 | AAGGCTTGTAGATAGTATTGTTTCATGGTCCAAAG SEQ ID NO: 288 | GTCATTACTACTGTACAAGTTCCAT SEQ ID NO: 359 |

TABLE 4-continued

Optimized Primers and Probes for the Detection of influenza A, influenza B, 2009 influenza A/H1N1, oseltamivir-resistant influenza A/H1N1, oseltamivir-sensitive 2009 influenza A/H1N1, Process Control, 2009 influenza A/H3N2

| Group No. | Forward Primer | Probe | Reverse Primer |
|---|---|---|---|
| 115 | CTACTGCTAGCTTCATTTACAATGG SEQ ID NO: 218 | AAGGCTTGTAGATAGTATTGTTTC ATGGTCCAAAG SEQ ID NO: 289 | GTCATTACTACTGTACAAGTTCCAT SEQ ID NO: 360 |
| | | Seasonal H1N1 Resistance Genotyping | |
| 116 | ACCATAATGACCGATGGC SEQ ID NO: 361 CGCCTCGTACAAAATCTTCAA SEQ ID NO: 362 | ATTCCTCATAATAAAAATTGGGTG SEQ ID NO: 363 ATTCCTCATAATGAAAATTGGGTG SEQ ID NO: 364 | CCAGTTGTCCCTGCATAC SEQ ID NO: 365 AGGTCGATTTGAACCATGC SEQ ID NO: 366 |

A PCR primer set for amplifying an influenza A virus comprises SEQ ID NOS: 1 and 3. A probe for binding to an amplicon(s) of an influenza A virus comprises SEQ ID NO: 2.

A PCR primer set for amplifying an influenza B virus comprises at least one of the following sets of primer sequences: (1) SEQ ID NOS: 4, 6, 7 and 9; (2) SEQ ID NOS: 4 and 9-11; (3) SEQ ID NOS: 4, 6, 9 and 11; (4) SEQ ID NOS: 4, 7, 9 and 10; (5) SEQ ID NOS: 4, 7, 9 and 12; (6) SEQ ID NOS: 7, 9, 10 and 13; (7) SEQ ID NOS: 14, 16 and 18; (8) SEQ ID NOS: 4, 7 and 9; (9) SEQ ID NOS: 19 and 21; (10) SEQ ID NOS: 19 and 23; (11) SEQ ID NOS: 24-28; and (12) SEQ ID NOS: 24, 26, 27 and 29.

A probe for binding to an amplicon(s) of an influenza B comprises at least one of the following probe sequences: SEQ ID NOS: 5, 8, 15, 17, 20, 22 and 25.

A PCR primer set for amplifying a 2009 influenza A/H1N1 virus comprises at least one of the following sets of primer sequences: (1) SEQ ID NOS: 30-34; (2) SEQ ID NOS: 30 and 33-35; (3) SEQ ID NOS: 36, 38, 39 and 41; and (4) SEQ ID NOS: 42, 44, 45 and 47. A probe for binding to an amplicon(s) of a 2009 influenza A/H1N1 comprises at least one of the following probe sequences: SEQ ID NO: 31, 37, 40, 43 and 46

A PCR primer set for amplifying an oseltamivir-resistant or sensitive 2009 influenza A/H1N1 virus comprises at least one of the following sets of primer sequences: (1) SEQ ID NOS: 48, 50 and 51; (2) SEQ ID NOS: 48-52; (3) SEQ ID NOS: 50 and 52; (4) SEQ ID NOS: 53 and 55; (5) SEQ ID NOS: 57 and 59; and (6) SEQ ID NOS: 61 and 62. A probe for binding to an amplicon(s) of a oseltamivir-resistant 2009 influenza A/H1N1 comprises at least one of the following probe sequences: SEQ ID NOS: 49, 54, 56, 58, 60 and 63-67.

The probes can be molecular beacon probes, TaqMan® probes, BHQ+ probes, and/or probes modified with locked nucleic acids.

The probes of the present invention are not limited to the modifications described herein. The probes of the present invention may be modified or unmodified.

Any set of primers can be used simultaneously in a multiplex reaction with one or more other primer sets, so that multiple amplicons are amplified simultaneously.

Other Embodiments

Other embodiments will be evident to those of skill in the art. It should be understood that the foregoing detailed description is provided for clarity only and is merely exemplary. The spirit and scope of the present invention are not limited to the above examples, but are encompassed by the following claims. The contents of all references cited herein are incorporated by reference in their entireties.

What is claimed is:

1. A method of hybridizing an isolated nucleic acid consisting of: SEQ ID NO: 1 and an isolated nucleic acid consisting of: SEQ ID NO: 3 to an influenza A virus, comprising contacting the isolated nucleic acid sequences to a sample comprising the influenza A virus under conditions suitable for hybridization.

2. The method of claim 1, wherein the influenza A virus is selected from the group consisting of: a genomic sequence in a naturally occurring plasmid, a genomic sequence in a naturally occurring transposable element, a template sequence, and a sequence derived from an artificial construct.

3. The method of claim 1, further comprising isolating the hybridized influenza A virus.

4. The method of claim 1, further comprising sequencing the hybridized influenza A virus.

5. A method of producing a nucleic acid product, comprising contacting an isolated nucleic acid consisting of: SEQ ID NO: 1 and an isolated nucleic acid consisting of: SEQ ID NO: 3 to a sample comprising influenza viruses under conditions suitable for nucleic acid polymerization; and polymerizing the isolated nucleic acid sequences to a plurality of target sequences in the sample.

6. The method of claim 5, wherein the nucleic acid product is an amplicon produced using a forward primer consisting of SEQ ID NO: 1; and a reverse primer consisting of SEQ ID NO: 3.

7. A method for detecting influenza A in a sample, comprising:

a) contacting the sample with a forward primer consisting of: SEQ ID NO: 1; and a reverse primer consisting of: SEQ ID NO: 3 under conditions such that nucleic acid amplification occurs to yield an amplicon; and b) contacting the amplicon with a probe consisting of: SEQ ID NO: 2, under conditions such that hybridization of the probe to the amplicon occurs;

wherein hybridization of the probe is indicative of influenza A in the sample.

8. The method of claim 7, wherein the probe is labeled with a detectable label.

9. The method of claim 7, wherein the sample is selected from the group consisting of:

saliva, fluids collected from the ear, eye, mouth, and respiratory airways, sputum, tears, oropharyngeal swabs, nasopharyngeal swabs, throat swabs, nasopharyngeal aspirates, bronchoalveolar lavage fluid, skin swabs, nasal aspirates, nasal wash, and fluids and cells obtained by the perfusion of tissues of both human and animal origin.

10. The method of claim 7, wherein the sample is from a human.

11. The method of claim 7, wherein the sample is non-human in origin.

12. The method of claim 7, wherein the sample is derived from an inanimate object or environmental surface.

* * * * *

UNITED STATES PATENT AND TRADEMARK OFFICE
CERTIFICATE OF CORRECTION

PATENT NO. : 8,758,996 B2  
APPLICATION NO. : 12/887193  
DATED : June 24, 2014  
INVENTOR(S) : James R. Hully et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 121 days.

Signed and Sealed this  
Thirteenth Day of October, 2015

Michelle K. Lee  
*Director of the United States Patent and Trademark Office*